(12) United States Patent
Saeki et al.

(10) Patent No.: US 12,029,578 B2
(45) Date of Patent: Jul. 9, 2024

(54) SKIN DIAGNOSING DEVICE, SKIN CONDITION OUTPUTTING METHOD, PROGRAM, AND RECORDING MEDIUM

(71) Applicants: MEIJO UNIVERSITY, Aichi (JP); SHISEIDO COMPANY, LTD., Tokyo (JP)

(72) Inventors: Souichi Saeki, Osaka (JP); Yusuke Hara, Kanagawa (JP); Toyonobu Yamashita, Kanagawa (JP)

(73) Assignees: SHISEIDO COMPANY, LTD., Tokyo (JP); MEIJO UNIVERISTY, Nagoya (JP)

(*) Notice: Subject to any disclaimer, the term of this patent is extended or adjusted under 35 U.S.C. 154(b) by 1425 days.

(21) Appl. No.: 16/224,261

(22) Filed: Dec. 18, 2018

(65) Prior Publication Data
US 2019/0125247 A1    May 2, 2019

Related U.S. Application Data

(63) Continuation of application No. PCT/JP2017/022064, filed on Jun. 15, 2017.

(30) Foreign Application Priority Data

Jun. 20, 2016  (JP) .................. 2016-121492
May 17, 2017  (JP) .................. 2017-098372

(51) Int. Cl.
*A61B 5/00*     (2006.01)
*A61B 5/026*    (2006.01)
*A61B 10/00*    (2006.01)

(52) U.S. Cl.
CPC .............. *A61B 5/442* (2013.01); *A61B 5/00* (2013.01); *A61B 5/0064* (2013.01);
(Continued)

(58) Field of Classification Search
CPC ....... A61B 5/442; A61B 5/443; A61B 5/0064; A61B 5/0066; A61B 5/026
See application file for complete search history.

(56) References Cited

U.S. PATENT DOCUMENTS

| | | | | |
|---|---|---|---|---|
| 6,006,128 A * | 12/1999 | Izatt | .................. | A61B 5/0073 600/476 |
| 10,932,670 B2 * | 3/2021 | Smith | .............. | G01B 9/02025 |
| 2005/0171438 A1 * | 8/2005 | Chen | ................. | G01B 9/0201 600/425 |

FOREIGN PATENT DOCUMENTS

| | | |
|---|---|---|
| JP | 2007-500529 A | 1/2007 |
| JP | 2009-268640 A | 11/2009 |

(Continued)

OTHER PUBLICATIONS

Liang, et al., Biomechanical Properties of In Vivo Human Skin From Dynamic Optical Choherence Elastography IEEE Trans Biomed Eng 57(4): 953-959 (Apr. 2010) (Year: 2010).*

(Continued)

*Primary Examiner* — Rajeev P Siripurapu
(74) *Attorney, Agent, or Firm* — MUNCY, GEISSLER, OLDS & LOWE, P.C.

(57) ABSTRACT

A skin diagnosing device includes an optical unit including: an optical system that uses OCT; an optical mechanism to guide light from the optical unit to skin to scan the skin; a loading device to apply predetermined deformation energy to the skin; a control computation unit to compute tomographic distribution of predetermined status values relating to the skin by controlling driving of the loading device and the optical mechanism and processing optical interference signals output from the optical unit in response to the driving, to compute an evaluation value of the skin based on the tomographic distribution; and a display device to display the evaluation value of the skin. The control computation (Continued)

unit computes the evaluation value by computing mechanical characteristics and a blood flow condition of the skin as the status values and associating the mechanical characteristics and the blood flow condition at a cross-sectional position of the skin.

10 Claims, 26 Drawing Sheets

(52) U.S. Cl.
CPC ............ *A61B 5/0066* (2013.01); *A61B 5/026* (2013.01); *A61B 5/0261* (2013.01); *A61B 5/443* (2013.01); *A61B 10/00* (2013.01)

(56) References Cited

FOREIGN PATENT DOCUMENTS

| | | | |
|---|---|---|---|
| JP | 2013-188326 A | 9/2013 | |
| JP | 2016-11935 A | 1/2016 | |
| KR | 20160001890 A | 1/2016 | |
| WO | WO-2016002432 A1 * | 1/2016 | ............ A61B 10/00 |

OTHER PUBLICATIONS

Kennedy et al. Quantitative micro-elastography imaging of tissue elasticity using compression optical coherence elastography, Scientific Reports | 5:15538 (Oct. 2015) (Year: 2015).*

Ikunami et al., "Development Study on Tomographically Visualizing Method of Water Content and Mechanical Strain in Skin Tissue using Low Coherence Interferometer," The Japan Society of Mechanical Engineers, No. 11-1, Sep. 6, 2014, 5 pages.

Saeki et al., "Basic study on Micro-tomographic visualization of mechanical properties inside skin tissue using Suction-typed Dynamic Optical Coherence Straingraphy," The Japan Society of Mechanical Engineers, No. 14-1, Sep. 6, 2014, 4 pages.

Kusumoto et al., "Basic study on Tomographic Micro-visualizing System of Moisture Content inside Skin Tissue using Low Coherence Interferometer with 1400 nm band light source," The Japan Society of Mechanical Engineers, No. 15-69, Jan. 8, 2016, 5 pages.

Furukawa et al., "Basic Study on Micro-tomographic Visualization of Blood Flow in Microcirculation using High-Frequency Modulated Low Coherence Interferometer," The Japan Society of Mechanical Engineers, No. 16-1, Dec. 10, 2016, 4 pages.

Ikunami et al., "Development Study on Tomographically Visualizing Method of Water Content and Mechanical Strain in Skin Tissue using Low Coherence Interferometer," The Japan Society of Mechanical Engineers, No. 11-1, Sep. 10, 2011, 5 pages.

Furukawa et al., "Basic Study on Micro-tomographic Visualization of Blood Flow in Microcirculation using High-Frequency Modulated Low Coherence Interferometer," The Japan Society of Mechanical Engineers, No. 16-1, Sep. 10, 2016, 4 pages.

Choi et al., In Vivo monitoring of external pressure induced hemodynamics in skin tissue using optical coherence tomography angiography. Mar. 6, 2015 Optical Elastography and Tissue Biomechanics II, Proc. of SPIE vol. 9327, 8 pages.

* cited by examiner

FIG.4A
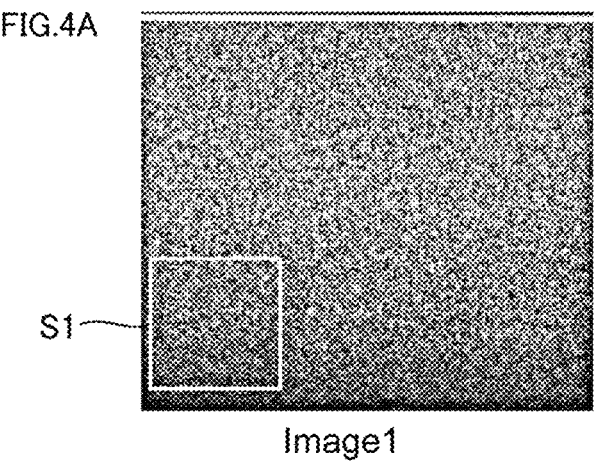
Image1
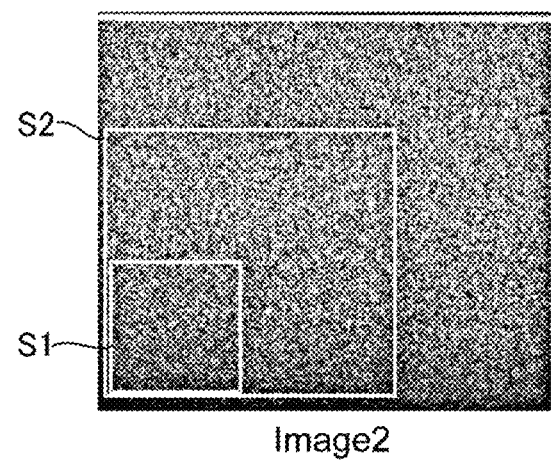
Image2
FIG.4B
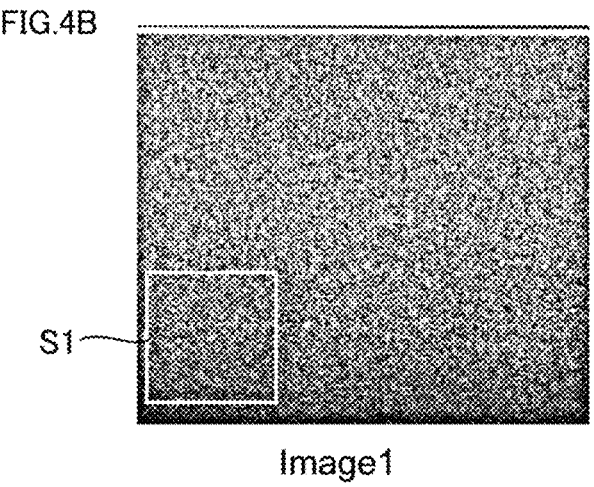
Image1
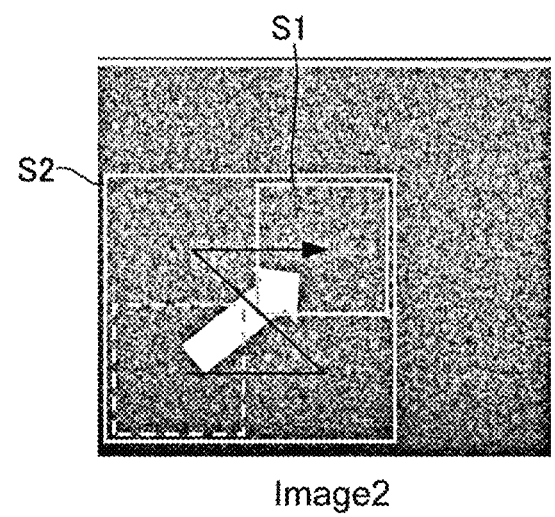
Image2
FIG.4C
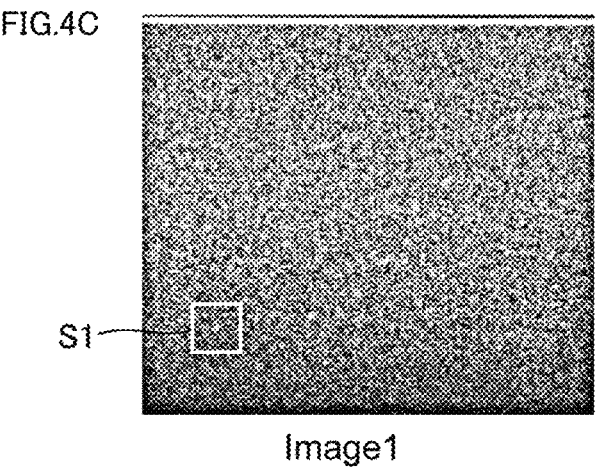
Image1
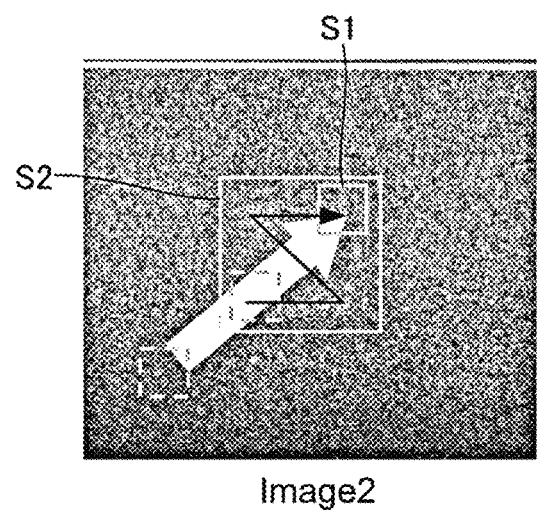
Image2

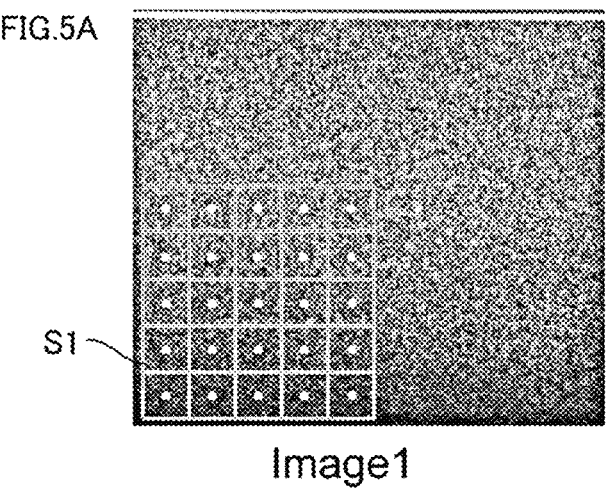
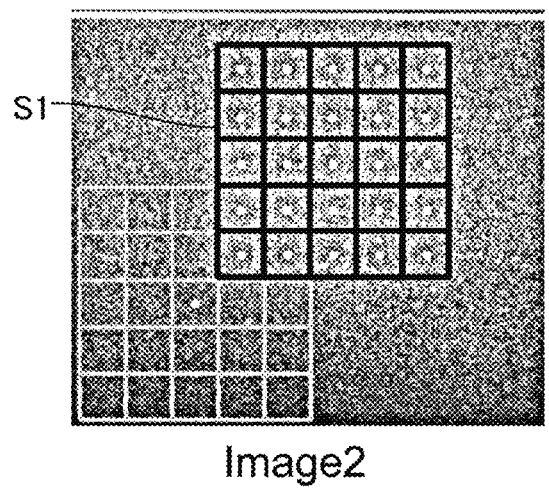
FIG.5A — Image1 / Image2
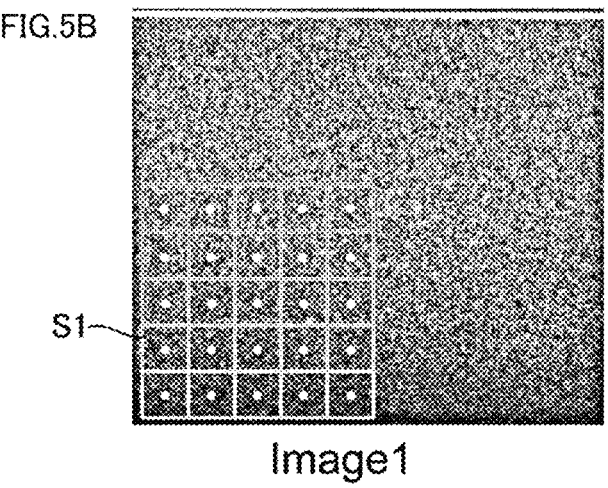
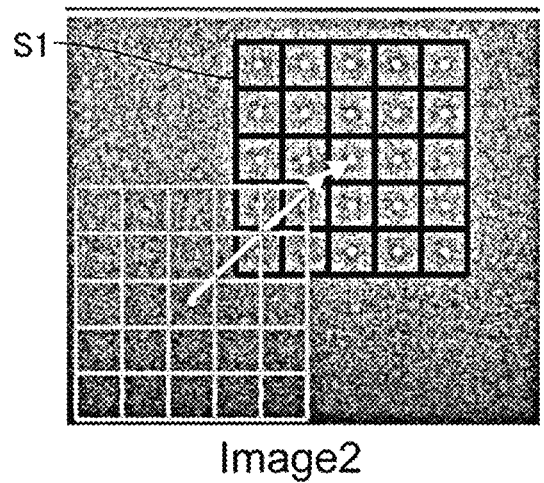
FIG.5B — Image1 / Image2
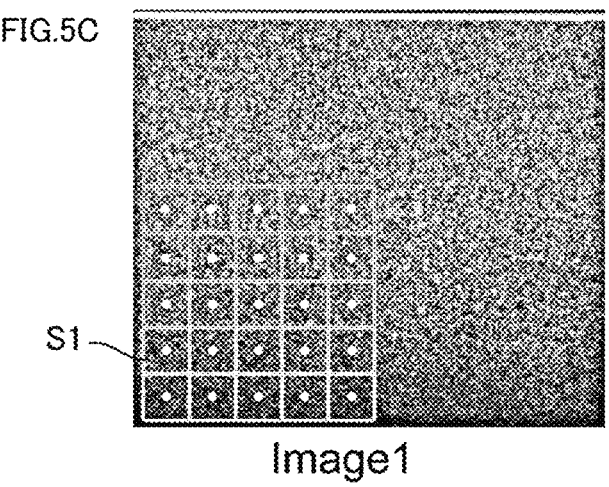
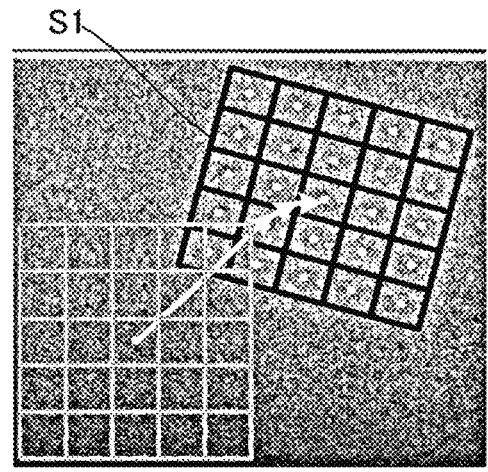
FIG.5C — Image1 / Image2

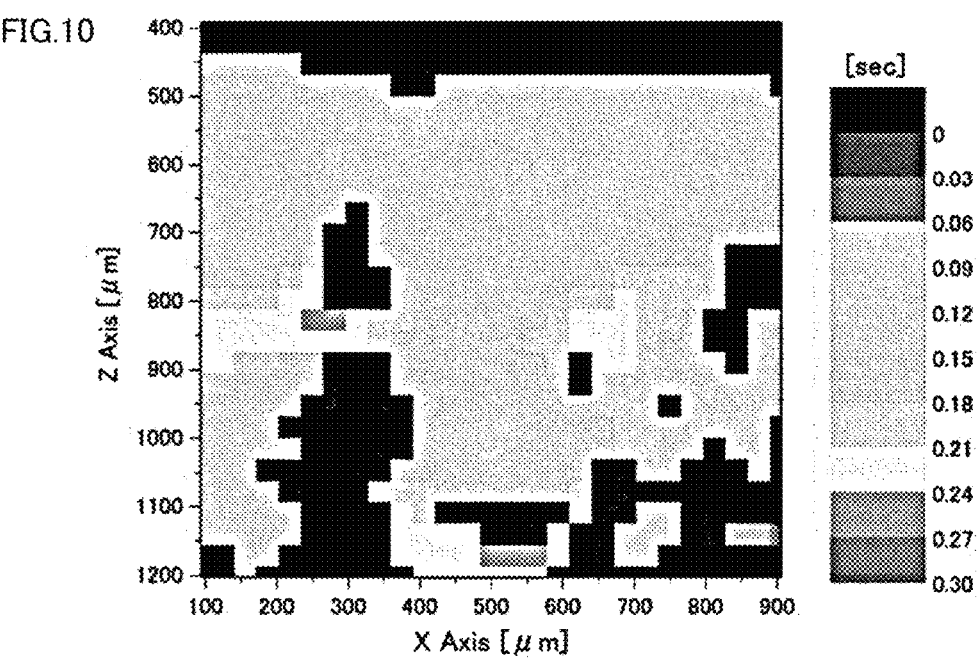

SKIN DIAGNOSING DEVICE, SKIN CONDITION OUTPUTTING METHOD, PROGRAM, AND RECORDING MEDIUM

CROSS-REFERENCE TO RELATED APPLICATIONS

This application is a continuation application of International Application No. PCT/JP2017/022064 filed on Jun. 15, 2017, which claims priority to and the benefit of Japanese Patent Application Nos. 2016-121492 and 2017-098372, filed on Jun. 20, 2016 and May 17, 2017, respectively. The contents of these applications are incorporated herein by reference in their entirety.

BACKGROUND OF INVENTION

1. Field

The present invention relates to a device and a method for diagnosing skin.

2. Description of Related Art

Skin tissue serves such important roles as preventing loss of moisture, thermoregulating through heat exchange with external environment, protecting a living body from physical irritation, and perceiving senses such as touch. The skin tissue is mainly constituted by three layers, which are epidermis, dermis, and subcutaneous tissue. Changes in the mechanical characteristics of the layers due to aging and environmental changes such as ultraviolet rays are considered causes of the symptoms of aging of the skin such as winkles and sagging. In addition, deterioration of microcirculatory function that controls the metabolic function of skin tissue is considered one of causes of the symptoms of aging. Thus, integrative evaluation of the mechanical characteristics and the circulatory function of skin can lead to effective skin care and anti-aging effects.

In relation to such diagnosis of skin, a method of analyzing skin condition by measuring three-dimensional shapes of sulcus cutis on a skin surface is known (refer to Patent Literature 1, for example). In addition, a method of measuring the mechanical characteristics of skin by sucking and unloading a particular site of skin and detecting a surface position of the skin is also known (refer to Patent Literature 2, for example).

RELATED ART LIST

Patent Literature 1: JP 2013-188326
Patent Literature 2: JP 2009-268640

The method of Patent Literature 1, however, measures the surface profile itself resulting from changes of skin tissue, but cannot perform diagnosis at a skin tissue level. The method of Patent Literature 2 enables measurement of the mechanical characteristics at the skin tissue level, but it is difficult to evaluate a skin condition in an integrative manner by this method alone.

SUMMARY OF INVENTION

In view of the above and other circumstances, one of objects of the present invention is to provide a device and a method for diagnosing a skin condition in various aspects and in an integrative manner.

An embodiment of the present invention relates to a skin diagnosing device. The skin diagnosing device includes: an optical unit including an optical system that uses optical coherence tomography (hereinafter referred to as the OCT); an optical mechanism to guide light from the optical unit to skin to scan the skin; a loading device to apply predetermined deformation energy to the skin; a control computation unit to compute tomographic distribution of predetermined status values relating to the skin by controlling driving of the loading device and the optical mechanism and processing optical interference signals output from the optical unit in response to the driving, to compute an evaluation value of the skin on the basis of the tomographic distribution; and a display device to display the evaluation value of the skin. The control computation unit computes the evaluation value by computing mechanical characteristics and a blood flow condition of the skin as the status values and associating the mechanical characteristics and the blood flow condition at a cross-sectional position of the skin.

Another embodiment of the present invention relates to a skin diagnosing method. The skin diagnosing method includes: a step of acquiring a tomographic image of skin by using the OCT; a step of computing mechanical characteristics and a blood flow condition of the skin on the basis of the tomographic image; a step of acquiring information for evaluating a condition of the skin by associating the mechanical characteristics and the blood flow condition at a cross-sectional position of the skin, and outputting the information.

Note that any combination of the aforementioned features, and any conversion of the expressions of the present invention into those of a method, a device, a system, a recording medium, a computer program, and the like are also effective as embodiments of the present invention.

According to the present invention, a device and a method for diagnosing a skin condition in various aspects and in an integrative manner are provided.

BRIEF DESCRIPTION OF DRAWINGS

FIGS. 4A to 4C schematically show procedures of a recursive cross-correlation method;

FIGS. 5A to 5C schematically show procedures of sub-pixel analysis;

FIG. 10 shows tomographic distribution of creep recovery time;

DETAILED DESCRIPTION

Figure 1:
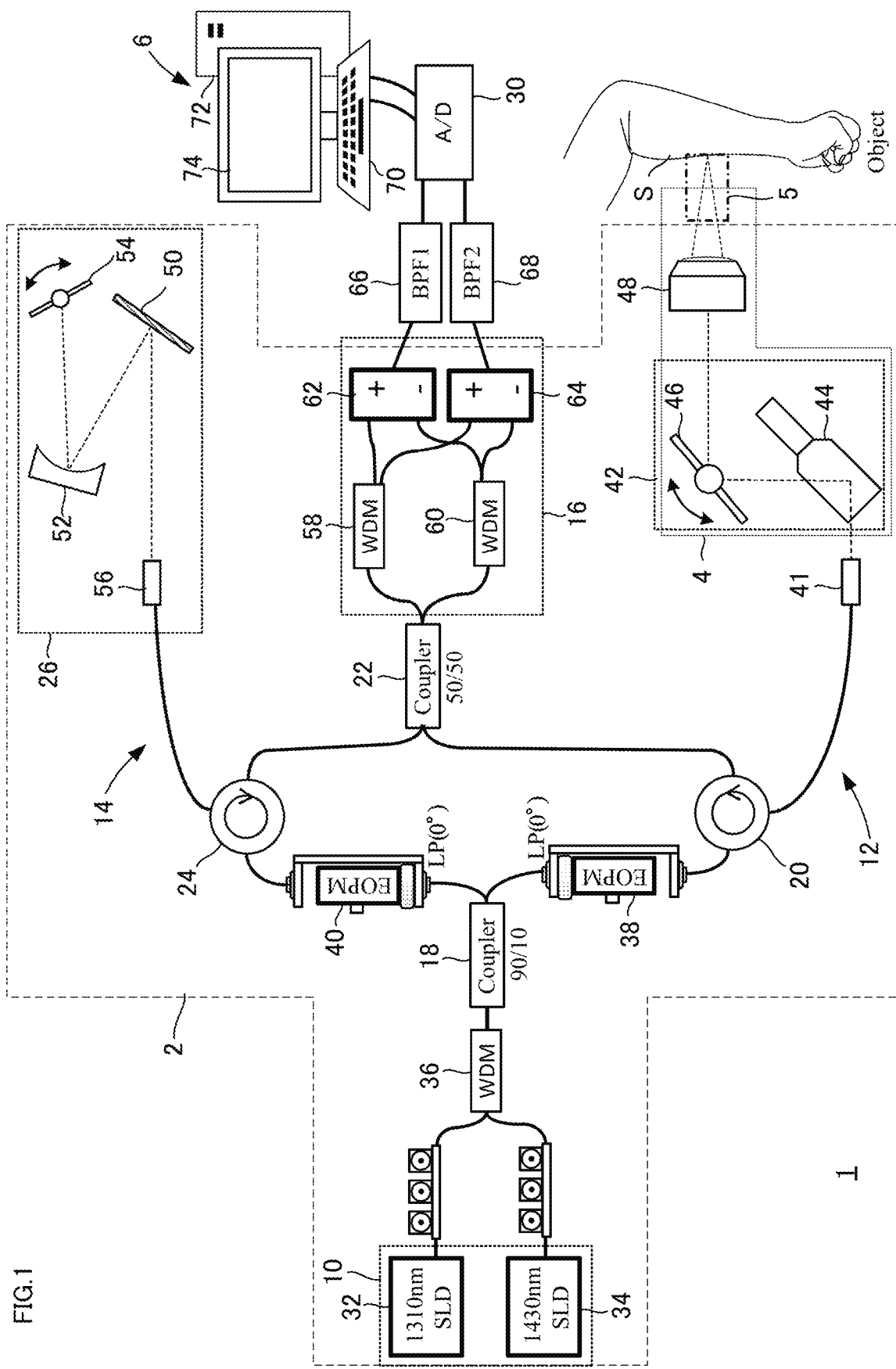
FIG. 1 is a diagram schematically illustrating a configuration of a skin diagnosing device according to an embodiment.

An embodiment of the present invention relates to a skin diagnosing device. The skin diagnosing device has a function of controlling tomographic measurement of skin using the OCT, a function of acquiring a tomographic image of the skin obtained through the tomographic measurement, a function of computing mechanical characteristics of the skin and a blood flow condition under the skin on the basis of the acquired tomographic image, and a function of acquiring and outputting information for diagnosing the skin by associating the mechanical characteristics with the blood flow condition at the cross-sectional position of the skin. More specifically, the skin diagnosing device has a function of computing tomographic distributions of change in mechanical feature value and change in blood flow condition with deformation of the skin, and outputting information for diagnosing the skin on the basis of the ratio of the change in blood flow condition to the change in mechanical feature value.

The skin diagnosing device captures a tomographic image of a specific site of skin by using the OCT while applying predetermined deformation energy (load) to the specific site, and outputs an evaluation value for skin diagnosis based on the mechanical behavior of skin tissue and a change in the blood flow condition with the behavior. The mechanical behavior may be obtained as "a change in mechanical feature value," which is a mechanical characteristic, by tomographic measurement.

Note that the "mechanical feature value" may be obtained on the basis of spatial distribution of deformation vectors (motion vectors) of skin tissue. The "mechanical feature value" may be a deformation vector itself, for example. In addition, the "change in mechanical feature value" may be a deformation rate vector obtained as a time derivative of a deformation vector, or a strain rate tensor further obtained as a space derivative of the deformation rate vector. Alternatively, a deformation rate vector or a strain rate tensor may be used as the "mechanical feature value" and a time derivative thereof may be used as "a change in mechanical feature value." The "blood flow condition" may be a blood flow velocity (flow rate) or the form (shape and arrangement) of a network of blood vessels. The "blood flow condition" may be defined as a "hemodynamic status."

The mechanical feature value and the blood flow condition are tomographically measured in the process of computation of the evaluation value. The evaluation value may be displayed as a tomographic measurement value associated with the position of skin tissue, or may be displayed as a value of integrative evaluation of a specific area or an entire area of skin based on the tomographic measurement value. Display of such an evaluation value on a display device allows a physician or the like to see the evaluation value for diagnosis of skin.

The skin diagnosing device includes an optical unit, an optical mechanism, a loading device, and a control computation unit. The optical unit includes an OCT optical system. The optical mechanism guides light from the optical unit to scan the skin. Tomographic measurement using the OCT can be performed in microscale, but may also be performed in nanoscale depending on desired resolution. The loading device applies predetermined deformation energy (load) to the skin prior to acquisition of a tomographic image.

A method of applying load by the loading device may be based on a stress relaxation technique of placing a certain strain on an object to be measure (skin) and measuring changes of stress with time. Alternatively, the method may be based on a dynamic viscoelastic method of placing a dynamic strain on an object to be measured and measuring a maximum value of stress and a phase difference. Still alternatively, the method may be based on a creep method of applying stress of a certain magnitude to an object to be measured and measuring changes of strain with time. The application of load by the loading device changes the mechanical feature value of the skin. The blood flow condition of the skin changes with the change of the mechanical feature value.

The control computation unit controls driving of the loading device and the optical mechanism, and processes an optical interference signal output from the optical unit in response to the driving to compute tomographic distribution (cross-sectional distribution) of status values, which are preset for skin. The "status values" used herein may include the mechanical feature value and the blood flow condition described above. The control computation unit computes a change in mechanical feature value and a change in blood flow condition in association with a cross-sectional position of the skin, for example. The control computation unit then computes an evaluation value on the basis of a degree of the change in blood flow condition with respect to the change in mechanical feature value.

According to this embodiment, the result of tomographic measurement using the OCT is used for outputting information for evaluating the skin condition on the basis of the degree of the change in the blood flow condition with respect to the change in the mechanical feature value of the skin. The output information based on correlation (association) between the mechanical characteristics and the blood flow characteristics is obtained, which enables diagnosis of skin condition in various aspects and in an integrative manner. The measurement using the OCT is employed, which enables tomographic measurement of the mechanical feature value and the blood flow condition at each of the levels of the respective layers of skin tissue. Regarding the latter, in particular, in view of the fact that information on capillaries is included, the employment of the OCT, which obtains information in microscale, is significant.

The control computation unit may compute a degree of deformation of a network of blood vessels as the degree of the change in blood flow condition. For example, in a case where strain is placed on skin and a network of blood vessels at the corresponding position deforms accordingly, the control computation unit may determine the skin condition to be good if the deformation of the network of blood vessels follows a change in strain quickly, and calculate how good the skin condition is as the evaluation value. In a case where the deformation of the network of blood vessels is delayed with respect to the change in strain, the control computation unit may determine that the skin condition is bad (has room for improvement), and calculate how bad the skin condition is as the evaluation value.

Alternatively, the control computation unit may compute a degree of a change in blood flow velocity as the degree of the change in blood flow condition. For example, in a case where strain is placed on skin and the blood flow velocity at the corresponding position changes accordingly, the control computation unit may determine the skin condition to be good if the change in blood flow velocity follows a change in strain quickly, and calculate how good the skin condition is as the evaluation value. In a case where the change in blood flow velocity is delayed with respect to the change in strain, the control computation unit may determine that the skin condition is bad (has room for improvement), and calculate how bad the skin condition is as the evaluation value. The display device visually displays the calculated evaluation value.

More specifically, the control computation unit may compute a displacement related vector associated with a cross-sectional position of skin as the mechanical feature value on the basis of tomographic image data acquired by processing an optical interference signal, and compute the evaluation value on the basis of the degree of a change in blood flow condition with respect to the degree of a change in displacement related vector. In this case, the control computation unit may compute, as the displacement related vector, a deformation rate vector or a strain rate tensor obtained as a space derivative of the deformation rate vector.

The control computation unit may further compute a change in water content (the amount of moisture) of the skin resulting from application of deformation energy (load) in association with the cross-sectional position of the skin, and compute the evaluation value on the basis of the degrees of the changes in blood flow condition and water content (the amount of moisture) with respect to the change in mechanical feature value.

Alternatively, the control computation unit may compute the evaluation value on the basis of how good or bad the mechanical characteristics are with respect to the blood flow condition. For example, the control computation unit may calculate a network of blood vessels of skin, and calculate the evaluation value on the basis of distribution of mechanical characteristics (elasticity or viscoelasticity) near the network of blood vessels. Specifically, when the elasticity or viscoelasticity near blood vessels (such as capillaries) is lower than a predetermined reference value (that is, when the skin tissue of the site is hardened), an evaluation value indicating that deterioration (aging) of the skin has been advancing can be displayed.

In addition, a skin diagnosing method using the techniques described above may be developed. This method may include a process of acquiring a tomographic image of skin by using the OCT, a process of computing the mechanical characteristics and the blood flow condition of the skin on the basis of the tomographic image, and a process of acquiring information for evaluating the condition of the skin by associating the mechanical characteristics and the blood flow condition at the cross-sectional position of the skin, and outputting the information. Specifically, the method may include a process of outputting information for evaluating the condition of the skin on the basis of the degree of the change in blood flow condition with respect to the change in mechanical feature value accompanying the deformation of the skin.

In addition, a skin diagnosis program using the techniques described above may be built. This program can cause a computer to perform a function of acquiring a tomographic image of skin by using the OCT, a function of computing the mechanical characteristics and the blood flow condition of the skin on the basis of the tomographic image, and a function of acquiring information for diagnosing the skin by associating the mechanical characteristics and the blood flow condition at the cross-sectional position of the skin, and outputting the information. Specifically, the program may cause the computer to perform a function of outputting information for evaluating the condition of the skin on the basis of the degree of the change in blood flow condition with respect to the change in mechanical feature value accompanying the deformation of the skin. The program may be recorded on a computer-readable recording medium.

In addition, in a case where a pressing load is applied as the deformation energy to skin, a light-transmitting elastic member may be located between a pressing mechanism and the skin. The loading device applies the pressing load to skin via the elastic member. The optical mechanism directs and receives light through the elastic member. A load detecting unit is capable of detecting a load applied to the elastic member as a pressing load applied to a skin surface. Such a configuration allows detection of changes in the load applied during the process of deformation of skin in real time, and achieves an object of performing accurate evaluation for skin diagnosis in real time.

The control computation unit computes tomographic distribution of change in mechanical feature value accompanying deformation of skin, and computes an evaluation value the skin on the basis of the tomographic distribution. The control computation unit computes a change in mechanical feature value of skin resulting from application of a pressing load in association with the cross-sectional position of the skin, and computes an evaluation value on the basis of the degree the change in mechanical feature value with respect to a change in the pressing load.

An example according to the present embodiment will now be described in detail with reference to the drawings.

EXAMPLE

FIG. 1 is a diagram schematically illustrating a configuration of the skin diagnosing device according to the example. The skin diagnosing device according to the example tomographically measures skin tissue in microscale, and enables evaluation of the skin condition (such has skin evaluation). The OCT is used for the tomographic measurement.

As illustrated in FIG. 1, the skin diagnosing device 1 includes an optical unit 2 including an optical system using the OCT, an optical mechanism 4 connected with the optical unit 2, a loading device 5 for applying a load for diagnosis to skin S, and a control computation unit 6 that performs arithmetic processing on the basis of optical coherence data obtained using the OCT. While an optical system based on a Mach-Zehnder interferometer is presented as the optical unit 2 in the example illustrated in FIG. 1, other optical systems such as a Michelson interferometer may alternatively be used.

While time domain OCT (TD-OCT) is used as the OCT in this example, other types of OCT such as swept source OCT (SS-OCT) or spectral domain OCT (SD-OCT) may be used instead. The SS-OCT is preferable in that high time resolution and high position detecting accuracy are achieved since mechanical optical delay scanning such as reference mirror scanning is not required.

The optical unit 2 includes a light source 10, an object arm 12, a reference arm 14, and an optical detection device 16. The respective optical components are connected with one another by optical fibers. Light emitted from the light source 10 is split by a coupler 18 (beam splitter). One beam from the coupler 18 becomes object light, which is guided to the object arm 12, and the other becomes reference light, which is guided to the reference arm 14. The object light guided to the object arm 12 is then guided to the optical mechanism 4 via a circulator 20, and directed to skin S that is an object to be measured. The object light is reflected as backscattered light at the surface and a cross section of the skin S, returned to the circulator 20, and then guided to a coupler 22.

Meanwhile, the reference light guided to the reference arm 14 is then guided to an optical mechanism 26 via a circulator 24. The reference light is reflected by a resonant mirror 54 of the optical mechanism 26, returned to the circulator 24, and then guided to the coupler 22. Thus, the object light and the reference light are combined (superimposed) by the coupler 22, and interference light of the object light and the reference light is detected by the optical detection device 16. The optical detection device 16 detects the interference light as an optical interference signal (a signal indicating interference light intensity). The optical interference signal is input to the control computation unit 6 via an AD converter 30.

The control computation unit 6 performs control of the entire optical system of the optical unit 2, drive control of the optical mechanisms 4 and 26 and the like, and arithmetic processing for outputting images using the OCT. Command signals from the control computation unit 6 are input to the optical mechanisms 4 and 26 and the like via a DA converter, which is not illustrated. The control computation unit 6 processes the optical interference signal output from the optical unit 2 on the basis of the driving of the optical mechanisms 4 and 26, and acquires a tomographic image of an object (skin S) to be measured using the OCT. The control computation unit 6 then computes tomographic distribution of a specific physical quantity inside the object on the basis of the tomographic image data by a technique described later.

This will be described in more detail below.

The light source 10 includes two light sources 32 and 34 having different center wavelengths from each other so as to allow detection of the amount of moisture of skin. These light sources are broadband light sources constituted by super luminescent diodes (hereinafter referred to as "SLDs"). The light source 32 is a light source with a 1310-nm wavelength band, and the light source 34 is a light source with a 1430-nm wavelength band. The control computation unit 6 can cause both of the light sources 32 and 34 to operate concurrently, but can also cause only one of the light sources 32 and 34 depending on the physical quantity to be measured.

A wavelength division multiplexing (WDM) spectral element 36 is provided between the light source 10 and the coupler 18. Light beams emitted from the light sources 32 and 34 are combined by the spectral element 36 and guided to the coupler 18.

An electro-optic phase modulator (EOPM) 38 is provided between the coupler 18 and the circulator 20. Similarly, an EOPM 40 is provided between the coupler 18 and the circulator 24. These EOPMs are capable of generating radio frequency carrier signals by linearly varying voltages applied thereto.

The optical mechanism 4 is included in the object arm 12. Light having passed through the circulator 20 is guided to the optical mechanism 4 via a collimator lens 41. The optical mechanism 4 includes a mechanism for guiding light from the optical unit 2 to scan the object (skin S), and a drive unit (actuator) for driving the mechanism. In this example, the optical mechanism 4 includes a Galvano system 42.

The Galvano system 42 includes a fixed mirror 44 and a galvanometer mirror 46. An object lens 48 is located to face the skin S (object). Light incident on the object arm 12 via the coupler 18 is scanned in the x-axis direction and the y-axis direction by the two-axis galvanometer mirror 46, and directed to the skin S. Light reflected by the skin S is returned as object light to the circulator 20, and guided to the coupler 22.

The optical mechanism 26 is a rapid scanning optical delay line (RSOD) mechanism included in the reference arm 14. The optical mechanism 26 includes a diffraction grating 50, a concave mirror 52, and the resonant mirror 54. Light having passed through the circulator 24 is guided to the optical mechanism 26 via a collimator lens 56. The light is split by the diffraction grating 50 according to wavelength, and focused on the resonant mirror 54 by the concave mirror 52. Rapid optical scanning is possible by turning the resonant mirror 54 by minute angles. Light reflected by the resonant mirror 54 is returned as reference light to the circulator 24 and guided to the coupler 22. The light is then superimposed with the object light, and sent as interference light to the optical detection device 16.

The optical detection device 16 includes WDM spectral elements 58 and 60, and photodetectors 62 and 64. 1310-nm-wavelength-band light of the interference light obtained through the coupler 22 is guided to the spectral element 58, and detected as an optical interference signal by the photodetector 62. The optical interference signal passes through a bandpass filter (BPF) 66 and the AD converter 30, and is then input to the control computation unit 6. Meanwhile, 1430-nm-wavelength-band light is guided to the spectral element 60, and detected as an optical interference signal (OCT interference signal) by the photodetector 64. The optical interference signal is input to the control computation unit 6 via a BPF 68 and the AD converter 30.

The control computation unit 6 is constituted by a personal computer in this example, and includes an input device 70 for receiving various user inputs, an arithmetic processing unit 72 that performs arithmetic processing according to computation programs for image processing, and a display device 74 that displays computation results. The arithmetic processing unit 72 includes a CPU, a ROM, a RAM, a hard disk, and the like, and uses the hardware and software to perform control of the entire optical unit 2 and arithmetic processing for image output based on results of optical processing.

Figure 2:
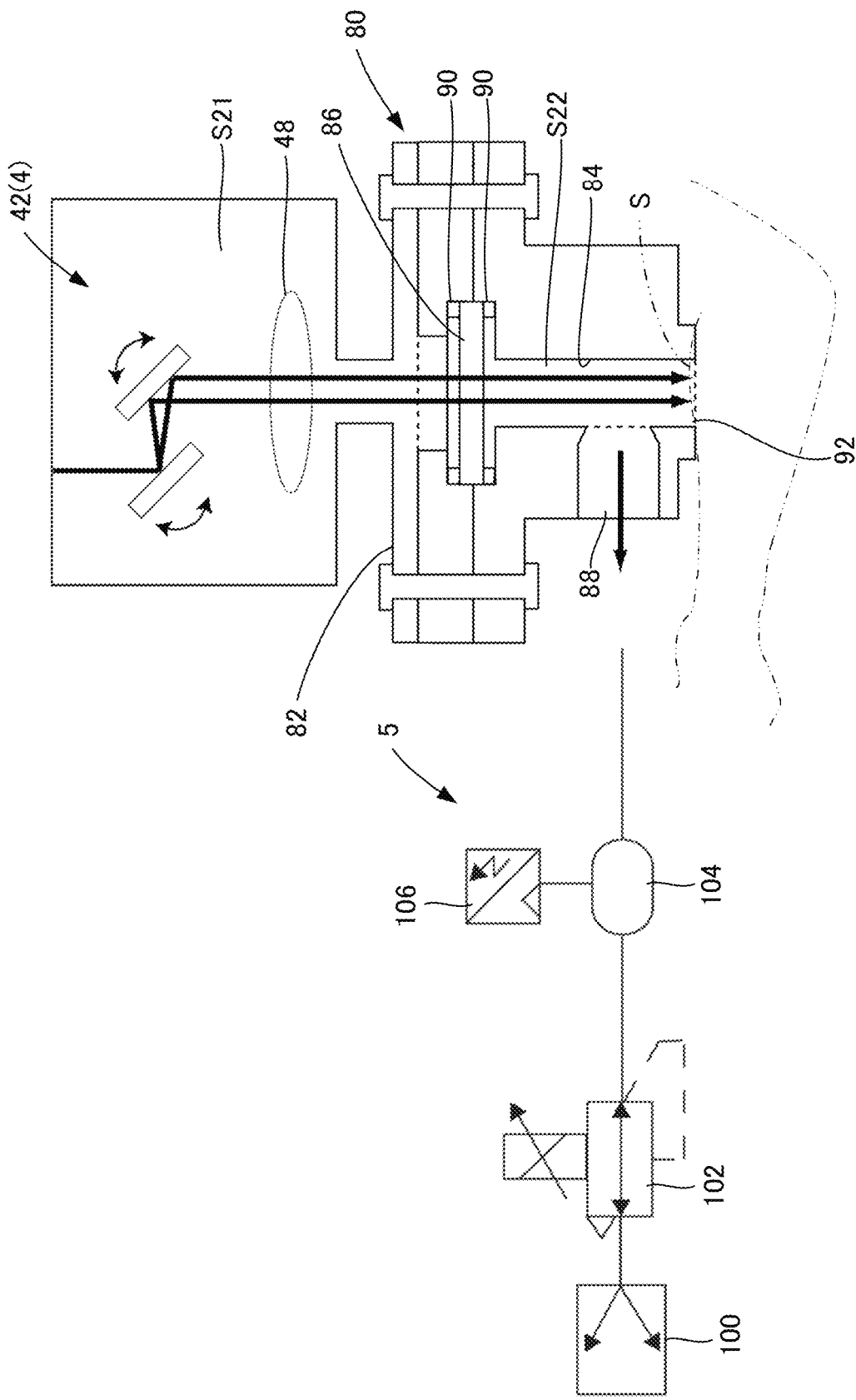
FIG. 2 is a diagram schematically illustrating a configuration of a loading device.

FIG. 2 is a diagram schematically illustrating a configuration of the loading device 5.

The loading device 5 has a configuration that applies a suction load to a site of skin S to be measured. A probe 80 for skin diagnosis is provided at an end of the optical mechanism 4. The loading device 5 is connected with the probe 80. An upper half part of the probe 80 functions as the optical mechanism 4, and a lower half part thereof functions as the loading device 5. The probe 80 has a body 82 made of metal. An internal passage 84 is formed to extend through the body 82 in the axial direction.

A translucent glass 86 is disposed to partition the internal passage 84 at the center in the axial direction. The Galvano system 42 and the object lens 48 are located in a space S21 above the glass 86. A suction chamber 88, which is connected with the loading device 5, communicates with a space S22 beneath the glass 86. Packings 90 are provided on and under the glass 86, so that sealing is provided between the space S21 and the space S22. The glass 86 functions as an entrance window for OCT beams. The axis of the internal passage 84 is coincident with the optical axis of the object arm 12. A lower end opening of the internal passage 84 constitutes a suction port 92 placed on the skin S for diagnosis.

The loading device 5 includes a vacuum pump 100, a regulator 102, a reservoir 104, a pressure gauge 106, and the like. The regulator 102 controls pressure to a target value. The reservoir 104 suppresses fluctuation of the pressure at the suction port 92.

An arithmetic processing method for skin diagnosis will be described below.

In this example, tomographic distributions of the following parameters are computed in microscale by using the OCT prior to skin diagnosis: the mechanical characteristics, the blood flow velocity, the network of blood vessels, and the amount of moisture of skin. An evaluation value for evaluating skin condition is then calculated by integrating the results of the computation of these parameters. The principles of calculation of the respective parameters will be explained below.

(1) Mechanical Characteristics of Skin

Prior to calculation of the mechanical characteristics of skin, a mechanical feature value of the skin is computed. For obtaining the mechanical feature value, tomographic distribution of strain accompanying deformation of the skin. As described above, according to the OCT, object light (light reflected by the skin) having passed through the object arm 12 and reference light having passed through the reference arm 14 are combined and detected as an optical interference signal by the optical detection device 16. The control computation unit 6 acquires the optical interference signal as a tomographic image of the object (skin S) on the basis of the interference light intensity. While the tomographic distribution can also be computed two-dimensionally, three-dimensional computation of the tomographic distribution will be explained herein.

A coherence length $l_c$, which represents the resolution in the optical axis direction (depth direction) of the OCT is determined by an autocorrelation function of the light source. Herein, the coherence length $l_c$ is the half width at half maximum of the envelope of the autocorrelation function, and can be expressed by the following expression (1).

$$l_c = \frac{2\ln 2}{\pi}\left(\frac{\lambda_c^2}{\Delta\lambda}\right) \quad (1)$$

In the expression, $\lambda_c$ represents the center wavelength of a beam, and $\Delta\lambda$ represents the full width at half maximum of the beam.

In addition, the resolution in the direction perpendicular to the optical axis (beam scanning direction) is ½ of a beam-spot diameter D on the basis of the focusing performance of a focusing lens. The beam-spot diameter $\Delta\Omega$ can be expressed by the following expression (2).

$$\Delta\Omega = \frac{4\lambda_c}{\pi}\left(\frac{f}{d}\right) \quad (2)$$

In the expression, d represents the diameter of a beam incident on the focusing lens, and f represents the focal point of the focusing lens. Although the resolution of the OCT is limited in this manner, this example enables tomographic measurement of strain in microscale by introducing sub-pixel analysis, which will be described later, and the like. Detailed explanation will be provided below.

First, a method of calculating three-dimensional strain distribution using the OCT will be explained. Herein, an FFT-based cross-correlation method is applied to two three-dimensional OCT images of an object acquired before and after deformation of the object to calculate distribution of deformation vector. For calculation of the deformation vector distribution, a recursive cross-correlation method of repeating cross-correlation is applied. This is a technique of applying a cross-correlation method by referring to deformation vectors calculated at low resolution, and limiting a search region while hierarchically reducing an interrogation region (subset, inspection region). This enables high-resolution deformation vectors to be obtained. Furthermore, an adjacent cross-correlation multiplication of multiplying correlation value distributions of adjacent interrogation regions is used as a method for reducing speckle noise. Correlation value distribution with a higher SNR obtained by the multiplication is then searched for a maximum correlation value.

In microscale deformation analysis, sub-pixel accuracy of deformation vectors is important. Thus, sub-pixel analysis methods including an upstream gradient method using an intensity gradient and an image deformation method based on expansion/contraction and shear are used to achieve high accuracy detection of deformation vectors. Note that the "upstream gradient method" used herein is one type of gradient methods (optical flow methods). The thus obtained deformation vector distribution is differentiated with respect to space for computation of strain tomographic distribution. In this case, the moving least square method is used to smooth a deformation quantity (displacement), and a three-dimensional strain tensor is calculated from a derivative of the smoothed deformation quantity. Hereinafter, the respective methods will be described in detail.

FFT-Based Cross-Correlation Method

Figure 3:
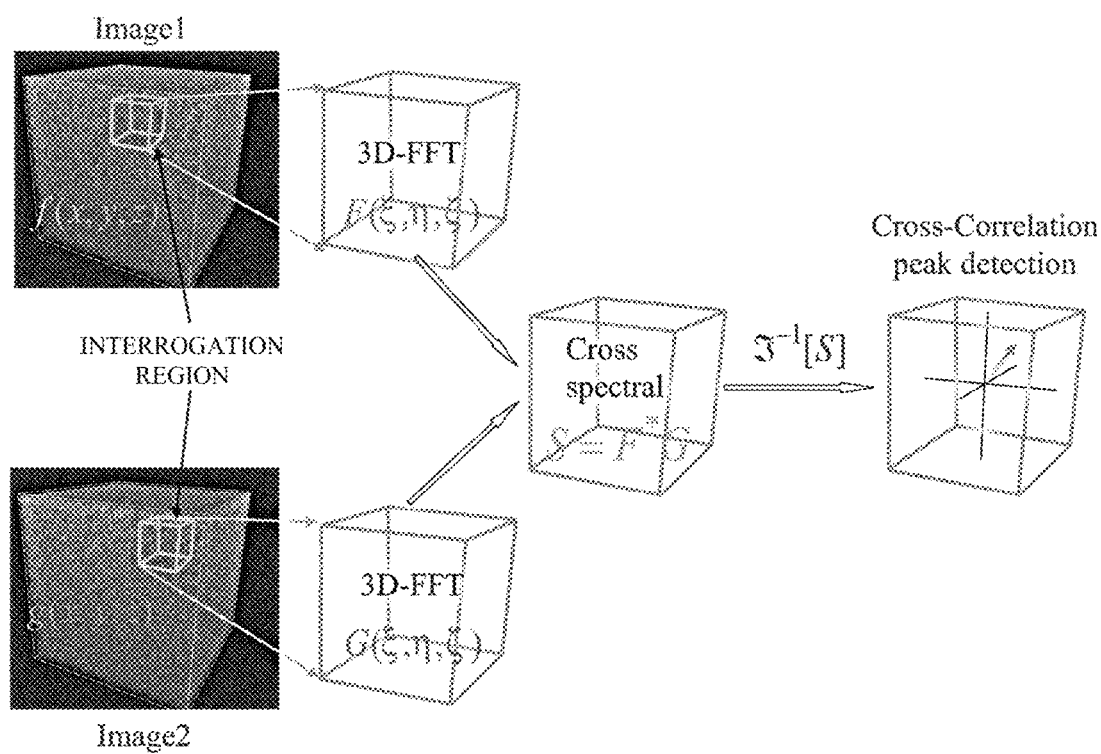
FIG. 3 schematically illustrates procedures of an FFT-based cross-correlation method.

FIG. 3 schematically illustrates procedures of the FFT-based cross-correlation method.

The FFT-based cross-correlation method is a method of evaluating similarity of local speckle patterns by using correlation values $R_{i,j,k}$, in which Fourier transform is used for calculation of the correlation values. An interrogation region of N×N×N pixels is set in a first image (Image1), a search region of the same size is set at the corresponding position in a second image (Image2), and correlation between these two regions is calculated. Directions perpendicular to incident light axis and the optical axis direction are referred to as X, Y, and Z, respectively. Intensity value patterns of the interrogation region in the first image and the search region in the second image are represented by $f(X_i, Y_j, Z_k)$ and $g(X_i, Y_j, Z_k)$, respectively, and Fourier transforms thereof are represented by $F\{f(X_i,Y_j,Z_k)\}$ and $F\{g(X_i, Y_j, Z_k)\}$, respectively. In this case, a cross-spectrum $S_{i,j,k}(\xi, \eta, \zeta)$ of the following expression (3) is obtained, and an inverse Fourier transform is applied to the obtained cross-spectrum, so that a cross-correlation function $R_{i,j,k}(\Delta X, \Delta Y, \Delta Z)$ is obtained as the following expression (4).

$$S_{i,j,k}(\xi, \eta, \zeta) = F^*\{f(X_i, Y_j, Z_k) - \overline{f}\}F\{g(X_i, Y_j, Z_k) - \overline{g}\} \quad (3)$$

$$R_{i,j,k}(\Delta X, \Delta Y, \Delta Z) = F^{-1}\{S_{i,j,k}(\xi, \eta, \zeta)\} \times$$
$$\left(\sum_{i=1}^{N_x}\sum_{j=1}^{N_y}\sum_{k=1}^{N_z}\{f(X_i, Y_j, Z_k) - \overline{f}\}^2\right)^{-\frac{1}{2}} \times \left(\sum_{i=1}^{N_x}\sum_{j=1}^{N_y}\sum_{k=1}^{N_z}\{g(X_i, Y_j, Z_k) - \overline{g}\}^2\right)^{-\frac{1}{2}} \quad (4)$$

In the expressions, $F^{-1}$ represents the inverse Fourier transform. In addition, $\overline{f}$ and $\overline{g}$ represent intensity mean values in the regions $f(X_i, Y_j, Z_k)$ and $g(X_i, Y_j, Z_k)$, respectively. Deviations from the mean values are used, and the correlation value is normalized. Coordinates at which the maximum correlation value is obtained are selected from the thus calculated correlation value distribution $R_{i,j,k}(\Delta X, \Delta Y, \Delta Z)$, and deformation vectors (motion vectors) with pixel accuracy are determined.

Recursive Cross-Correlation Method

FIGS. 4A to 4C schematically show procedures of the recursive cross-correlation method. For simplicity and convenience, FIGS. 4A to 4C are shown in two-dimensional representation. FIGS. 4A to 4C show processes of the recursive cross-correlation method. Each of FIGS. 4A to 4C shows tomographic images taken continuously using the OCT. A left image shows a tomographic image (Image1) taken first, and a right image shows a tomographic image (Image2) taken next.

As shown in FIG. 4A, in the OCT images taken continuously, an interrogation region S1 for similarity inspection is set in the first tomographic image (Image1), and a search region S2, which is a range for searching similarity, is set in the next tomographic image (Image2).

This technique employs the recursive cross-correlation method of repeating a cross-correlation process while reducing the interrogation region S1 to increase spatial resolution. Note that, in this example, the resolution is increased such that the spatial resolution is doubled. As shown in FIG. 4C, each of the interrogation region S1 and the search region S2 is hierarchically reduced to one-half in the X, Y, and Z directions, so that the spatial resolution is increased. Use of the recursive cross-correlation method prevents or reduces erroneous vectors that are frequently generated at high resolution. Such a recursive cross-correlation process increases the resolution of deformation vectors.

Adjacent Cross-Correlation Multiplication

In this example, the adjacent cross-correlation multiplication is introduced for determining an accurate maximum correlation value from highly-random correlation value distribution affected by speckle noise. According to the adjacent cross-correlation multiplication, the correlation value distribution $R_{i,j,k}(\Delta X, \Delta Y, \Delta Z)$ in the interrogation region S1 is multiplied by correlation value distribution for adjacent interrogation regions overlapping with the interrogation region S1 by an expression (5) below. The thus obtained new correlation value distribution $R'_{i,j,k}(\Delta X, \Delta Y, \Delta Z)$ is used to search for the maximum correlation value.

$$R'_{i,j,k}(\Delta X, \Delta Y, \Delta Z) = R_{i,j,k}(\Delta X, \Delta Y, \Delta Z) \times R_{i+\Delta i, j, k}(\Delta X, \Delta Y, \Delta Z) \times R_{i, j+\Delta j, k}(\Delta X, \Delta Y, \Delta Z) \times R_{i, j, k+\Delta k}(\Delta X, \Delta Y, \Delta Z) \quad (5)$$

As a result, the multiplication of the correlation values enables reduction in the randomness. Since the amount of information of interference intensity distribution is also reduced with the aforementioned reduction in size of the interrogation region S1, occurrence of multiple correlation peaks caused by speckle noise is considered to result in degradation in measurement accuracy. In contrast, since the displacements of adjacent boundaries are correlated, a high correlation value remains near the coordinates of the maximum correlation value. The introduction of the adjacent cross-correlation multiplication makes the maximum correlation peak clearer, improves the measurement accuracy, and accurately extracts displaced coordinates. In addition, the introduction of the adjacent cross-correlation multiplication at respective stages of the OCT prevents or reduces error propagation, and improves robustness to speckle noise. As a result, accurate deformation vector distribution (displacement distribution) is obtained even at high spatial resolution.

[Upstream Gradient Method]

FIGS. 5A to 5C schematically show procedures of sub-pixel analysis. For simplicity and convenience, FIGS. 5A to 5C are shown in two-dimensional representation. FIGS. 5A to 5C show processes of the sub-pixel analysis. Each of FIGS. 5A to 5C shows tomographic images taken continuously using the OCT. A left image shows a tomographic image (Image1) taken first, and a right image shows a tomographic image (Image2) taken next.

In this example, an upstream gradient method and an image deformation method are used for the sub-pixel analysis. Although a final displacement is calculated by the image deformation method to be described below, the upstream gradient method is applied prior to the image deformation method for the reason of convergence of calculations. The image deformation method and the upstream gradient method for detecting a sub-pixel displacement with high accuracy are applied under a condition where the interrogation region size is small and the spatial resolution is high. In a case where detection of a sub-pixel displacement by the image deformation method is difficult, the sub-pixel displacement is calculated by the upstream gradient method.

In the sub-pixel analysis, an intensity difference between before and after deformation at a point of interest is expressed by the intensity gradients of respective components and the displacement. Thus, the sub-pixel displacement can be determined by using the least-squares method from intensity gradient data in the interrogation region S1. In this example, for obtaining an intensity gradient, an upwind difference method that provides an upwind intensity gradient before sub-pixel deformation is used. Specifically, while there are various techniques for sub-pixel analysis, the gradient method that detects the sub-pixel displacement with high accuracy even under the condition where the interrogation region is small in size and the spatial resolution is high is used in this example.

The upstream gradient method is a technique for calculating displacement of a point of interest within the interrogation region S1 not just with pixel accuracy as shown in FIG. 5A but with sub-pixel accuracy as shown in FIG. 5B. Note that each square in FIGS. 5A to 5C represents one pixel. Although the pixels are actually significantly smaller than those in the shown tomographic images, the pixels are illustrated in a large size for convenience of explanation. The upstream gradient method is a technique of formulating a change in intensity distribution between before and after small deformation by using the intensity gradient and the displacement, and is expressed by the following expression (6) that calculates the Taylor expansion of small deformation $f(x+\Delta x, y+\Delta y, z+\Delta z)$ where f represents the intensity.

$$f_x(z,y,z)\Delta x + f_y(x,y,z)\Delta y + f_z(x,y,z)\Delta z = f(x+\Delta x, y+\Delta y, z+\Delta z) - f(x,y,z) \quad (6)$$

The expression (6) shows that the intensity difference at the point of interest between before and after deformation is expressed by the intensity gradient before the deformation and the displacement. Note that, since the displacement $(\Delta x, \Delta z)$ cannot be determined only by the expression (6), the displacement within the interrogation region S1 is assumed to be constant and the least-squares method is applied for the calculation.

In calculation of the displacement by using the expression (6), the intensity difference at each point of interest between before and after displacement on the right side of the expression (6) is obtained only uniquely. Thus, the accuracy of intensity gradient calculation is directly linked to the accuracy of the displacement. For differencing of the intensity gradient, first-order upwind difference is used. This is because a large amount of data will be required and the influence of contained noise, if any, will be great if a high-order difference is applied to differencing. This is also because a large amount of data outside of the interrogation region S1 will be used in a high-order difference based on a point in the interrogation region S1, which poses a problem that the obtained displacement will not be an amount of the interrogation region S1 itself.

In obtaining the intensity gradient, since it can be assumed that the displacement of an upwind intensity gradient before deformation causes an intensity difference at a point of interest, an upwind difference is applied before deformation. The term upwind used herein does not mean the actual displacement direction but means the direction of a sub-pixel displacement with respect to a pixel displacement, and the upwind direction is determined by applying parabolic approximation to the maximum correlation peak. Conversely, since it can be assumed that the reverse displacement of a downwind intensity gradient after deformation causes an intensity difference at a point of interest, a downwind difference is applied after deformation.

Two solutions are found by using the upwind difference before deformation and the downwind difference after deformation, and an average of the solutions is obtained. Furthermore, the intensity gradients before and after deformation are not actually on the same axis as the points of interest if the displacements are not along the axial direction, and gradients at shifted positions need to be obtained. Thus, the intensity gradient is estimated by intensity interpolation, so as to improve the accuracy. Basically, a position before (or after) deformation is estimated, and the gradient at the position is obtained by interpolation.

The position of a point of interest before (or after) deformation is obtained from the sub-pixel displacement $(\Delta x, \Delta y, \Delta z)$ when the parabolic approximation is applied. Eight coordinates surrounding the point of interest position are used, and the intensity gradient is calculated from the ratios of the intensities at the eight coordinates to the intensity at the point of interest. Specifically, the following expression (7) is used. The least-squares method is applied using the thus calculated intensity gradient and an intensity change to determine the displacement.

$$f_x(x,y,z) = \Delta y \Delta z \{f(z,y-1,z-1) - f(x-1,y-1,z-1)\} + (1-\Delta y) \\ \Delta z \{f(x,y,z-1) - f(z-1,y,z-1)\} + \Delta y(1-\Delta z)\{f(x,y-1, \\ z) - f(x-1,y-1,z)\} + (1-y)(1-\Delta z)\{f(z,y,z) - f(x-1,y,z)\} \quad (7)$$

Image Deformation Method

In the calculation of deformation vectors of the methods described above including the upstream gradient method, the shape of the interrogation region S1 has not been changed and remains square. In reality, however, since the interrogation region S1 is likely to be deformed with the deformation of the object, an algorithm based on small deformation of the interrogation region S1 needs to be introduced for calculation of deformation vectors with high accuracy. Thus, in this example, the image deformation method is introduced for calculation of deformation vectors with sub-pixel accuracy. Specifically, cross-correlation between the interrogation region S1 before deformation of the material and the interrogation region S1 after the deformation where expansion/contraction and shear deformation is considered is performed, and a sub-pixel deformation quantity is determined by repeated calculation based on the correlation value. Note that the expansion/contraction and shear deformation of the interrogation region S1 is linearly approximated.

More specifically, the computation is performed according to the following procedures. First, the bicubic interpolation is applied to the intensity distribution of the OCT image before the material deformation, to make the intensity distribution continuous. The bicubic interpolation is a technique of using a convolution function obtained by piecewise approximation of cubic polynomial function of a sinc function, to reproduce spatial continuity of intensity information. Since a point spread function dependent on an optical system is convolved in image measurement of intensity distribution, which is originally continuous, the originally continuous intensity distribution is reproduced by deconvolution using the sinc function. For interpolation of a single-axis, discrete signal f(x), a convolution function h(x) is expressed by the following expression (8).

$$h(x) \begin{cases} (a+2)|x|^3 - (a+3)|x|^2 + 1 & (|x| \le 1) \\ a|x|^3 - 5a|x|^2 + 8a|x| - 4a & (1 \le |x| \le 2) \\ 0 & (2 \le |x|) \end{cases} \quad (8)$$

Note that the shape of the interpolation function h(x) needs to be changed depending on the difference in OCT measurement condition. An algorithm in which a derivative a of the intensity interpolation function h(x) where x=1 is made to be variable and in which the shape of the intensity interpolation function h(x) is changeable by changing the value a is thus provided. In this example, the value a is determined on the basis of a result of verification by numerical experiment using a pseudo-OCT image. The image interpolation as described above allows an OCT intensity value to be obtained at each point in the interrogation region S1 where expansion/contraction and shear modification is considered.

The interrogation region S1 calculated in view of expansion/contraction and shear deformation thereof is deformed with displacement as shown in FIG. 5C. When it is assumed that coordinates (x,y,z) at an integer pixel position in an interrogation region S1 of an OCT image before skin tissue deformation are displaced to coordinates (x*,y*,z*) after the deformation, the values of x*, y*, and z* are expressed by the following expression (9).

$$\begin{cases} x^* = x + u + \Delta x + \frac{\partial u}{\partial x}\Delta x + \frac{\partial u}{\partial y}\Delta y + \frac{\partial u}{\partial z}\Delta z \\ y^* = y + v + \Delta y + \frac{\partial v}{\partial x}\Delta x + \frac{\partial v}{\partial y}\Delta y + \frac{\partial v}{\partial z}\Delta z \\ z^* = z + w + \Delta z + \frac{\partial w}{\partial x}\Delta x + \frac{\partial w}{\partial y}\Delta y + \frac{\partial w}{\partial z}\Delta z \end{cases} \quad (9)$$

In the expression (9), u, v, and w represent displacements in the x, y, and z directions, respectively, $\Delta x$, $\Delta y$, and $\Delta z$ represent displacements from the center of the interrogation region S1 to coordinates (x,y,z), $\partial u/\partial x$, $\partial v/\partial y$, and $\partial w/\partial z$ represent vertical strains in the x, y, and z directions, respectively, $\partial u/\partial y$, $\partial u/\partial z$, $\partial v/\partial x$, $\partial v/\partial z$, $\partial w/\partial x$, and $\partial w/\partial y$ represent shear strains in the x, y, and z directions, respectively. The Newton-Raphson method is used for numerical solution, and repeated calculation is carried out so that the correlation value derivative with twelve variables (u, v, w, $\partial u/\partial x$, $\partial u/\partial y$, $\partial u/\partial z$, $\partial v/\partial x$, $\partial v/\partial y$, $\partial v/\partial z$, $\partial w/\partial x$, $\partial w/\partial y$, and $\partial w/\partial z$) becomes 0, that is, so that the maximum correlation value is obtained. In order to increase the convergence of the repeated calculation, sub-pixel displacements obtained by the upstream gradient method are used for displacement initial values in the x, y, and z directions. When a Hessian matrix for a correlation value R is represented by H, and a Jacobi vector for the correlation value is represented by $\nabla R$, an update amount $\Delta P_i$ obtained at each repetition is expressed by the following expression (10).

$$\Delta P_i = -H^{-1}\nabla R \quad (10)$$

The determination of convergence is based on the fact that the asymptotic solution obtained at each repetition of calculation becomes sufficiently small near the convergent solution. In a region where the speckle pattern changes drastically, however, a correct convergent solution may not be obtained because the change cannot be tracked by linear deformation. In this case, the sub-pixel displacement obtained by the upstream gradient method is used in this example. The deformation vector distribution with sub-pixel accuracy is obtained in this manner.

The moving least square method is used for calculation of a strain amount. Specifically, the moving least square method is used to smooth a deformation quantity (displacement), and a strain tensor is calculated from a derivative of the smoothed deformation quantity.

FIGS. 6A, 6B, 7A and 7B show three-dimensional OCT images of skin.

Figure 6A:
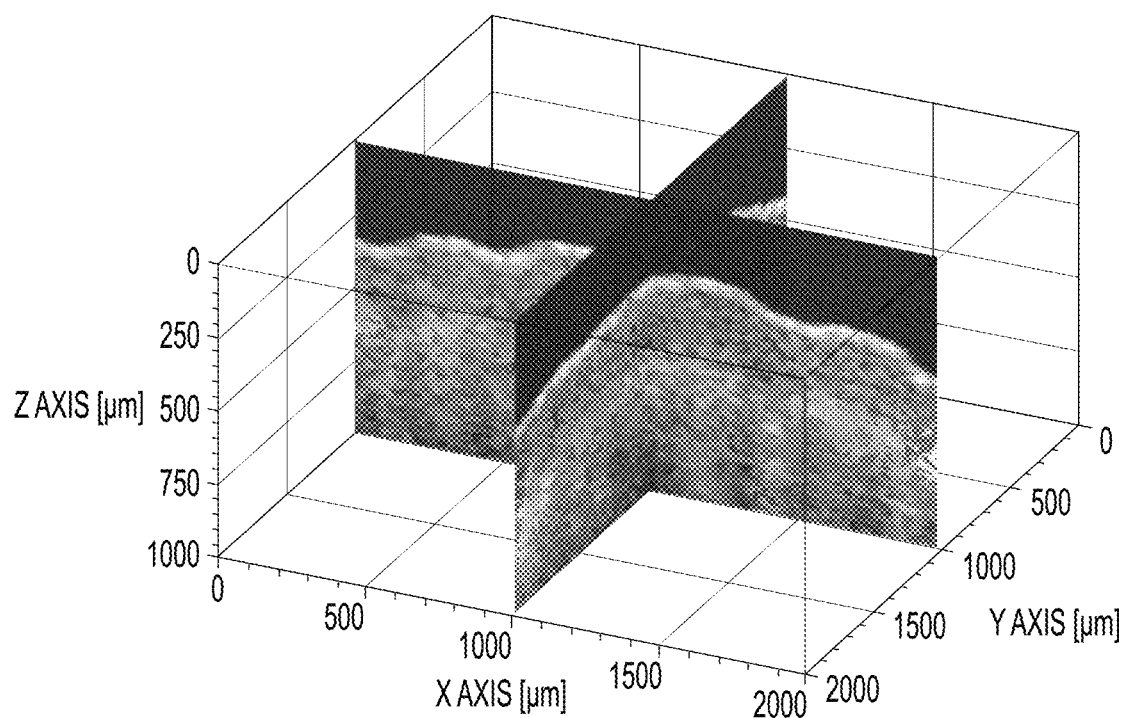
FIGS. 6A and 6B show three-dimensional OCT images of skin.
Figure 6B:
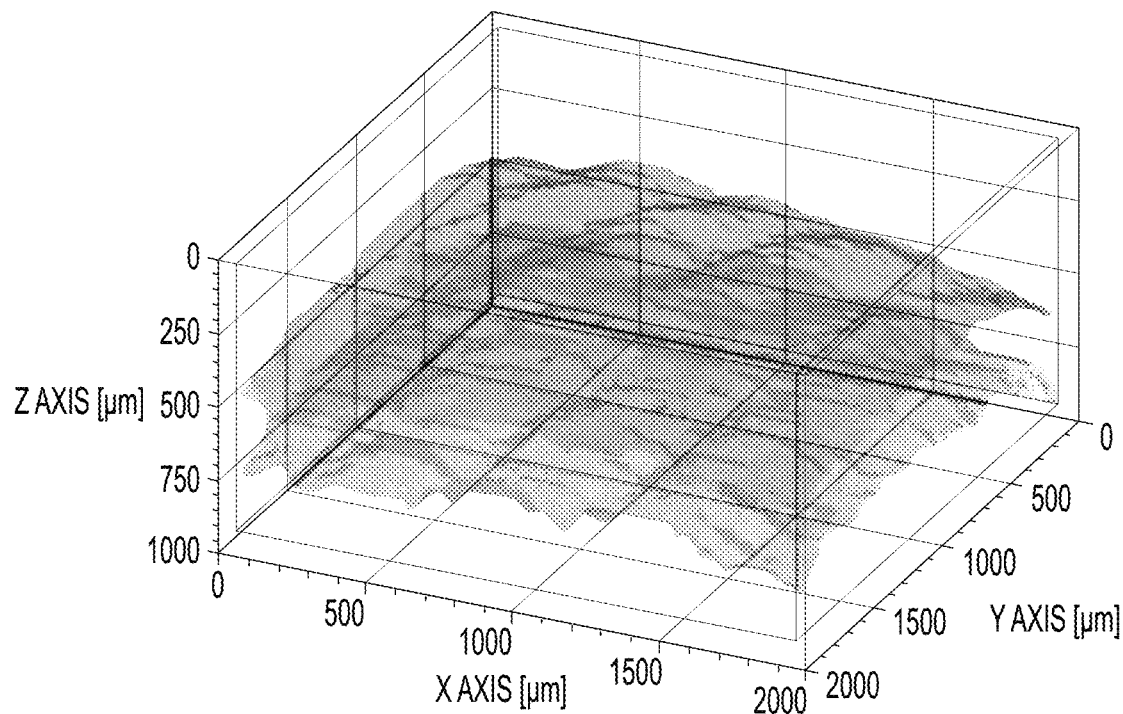

OCT beams are emitted to upper surfaces of the images. In FIG. 6A, a line with high intensity in the upper part corresponds to the skin surface, and a line with high intensity in the inside corresponds to a boundary between a horny layer and an epidermal living cell layer. FIG. 6B shows an extraction of the skin surface and the boundary between the horny layer and the epidermal living cell layer from the OCT image. Irregularities are observed on the skin surface. The meandering pattern of the surface and that of the boundary between the horny layer and the epidermal living cell layer are synchronous with each other, which is consistent with known pathology reports.

Figure 7A:
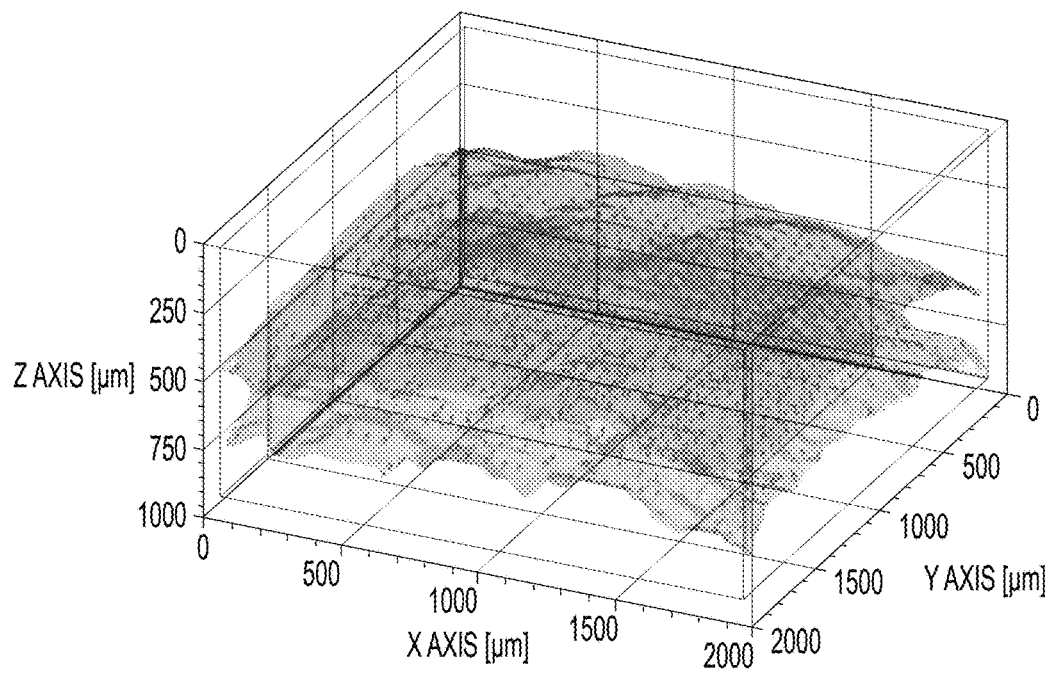
FIGS. 7A and 7B show three-dimensional OCT images of skin.
Figure 7B:
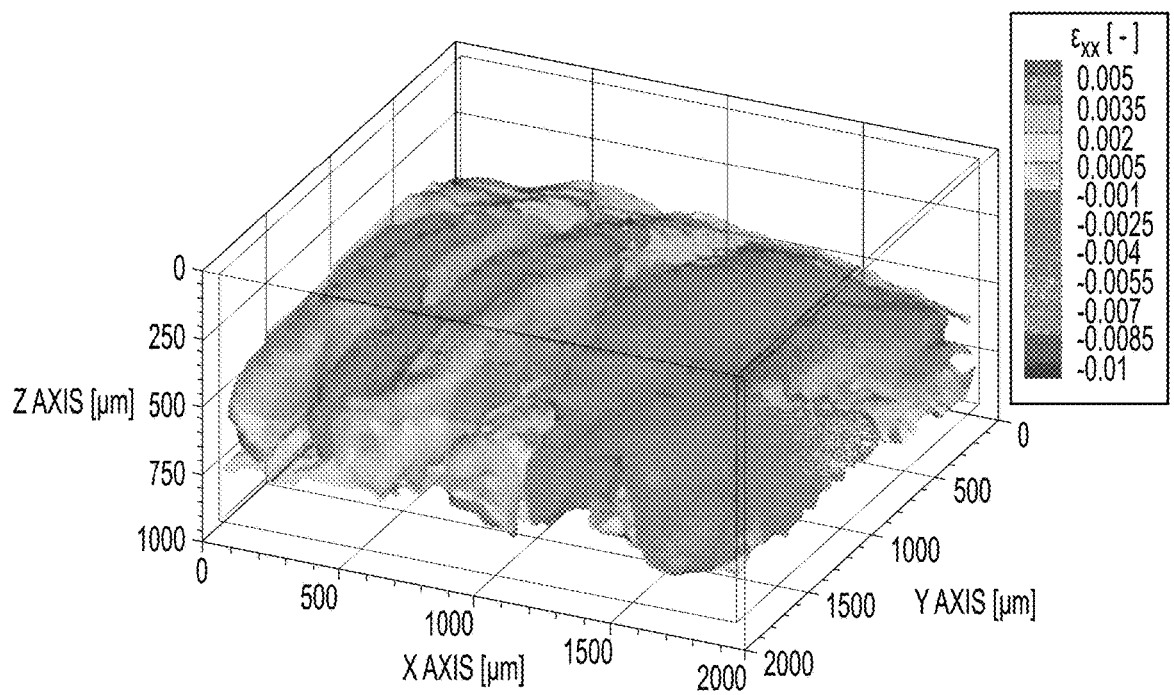

FIG. 7A shows tomographic distribution of deformation vector when a suction force acts on skin. It can be seen in FIG. 7A that deformation vectors are directed upward. It can be observed that the skin is raised with the suction. FIG. 7B shows a three-dimensional strain $\varepsilon xx$ in the x direction. In this manner, the OCT measurement allows the mechanical behavior of skin to be obtained.

Herein, the elasticity and the viscoelasticity of skin are calculated as the mechanical characteristics of skin. For the calculation, a predetermined load is applied to a site of skin to be measured, and tomographic measurement using the OCT is performed thereon. In this example, the creep method of applying stress of a certain magnitude and measuring changes of strain with time is used as a load applying method. Specifically, skin tissue is assumed to be a viscoelastic model, and a creep recovery time is calculated. The strain rate at creep recovery of the viscoelastic model is expressed by the following expression (11).

$$\dot{\varepsilon}(t) = A\exp\left\{-\frac{t}{\tau(k, c)}\right\} \quad (11)$$

In the expression (11), $\tau(k,c)$ represents the creep recovery time, k represents a modulus of elasticity, and c represents a coefficient of viscosity. $\tau(k,c)$ is larger as the model is more viscous, and smaller as the model is more elastic.

Figure 8:
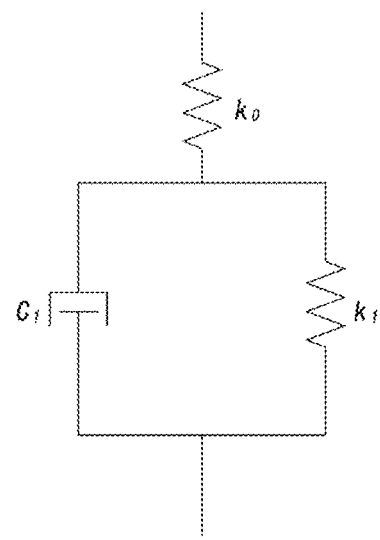
FIG. 8 is a diagram illustrating a viscoelastic model of skin tissue.

FIG. 8 is a diagram illustrating a viscoelastic model of skin tissue. In a case where skin tissue is assumed to be a three-element model as illustrated in FIG. 8, the creep recovery time $\tau(k,c)$ is expressed by a function of the modulus of elasticity and the coefficient of viscosity as expressions (12) and (13) below. Thus, the mechanical characteristics of skin tissue can be examined as a result of calculation of tomographic distribution $\tau(x,y,z)$ of the creep recovery time.

$$\dot{\varepsilon}(t) = \frac{a}{k_1}\exp\left\{-\frac{k_1}{c_1}t\right\} \quad (12)$$

$$\tau(k, c) = \frac{c_1}{k_1} \quad (13)$$

Figure 9A:
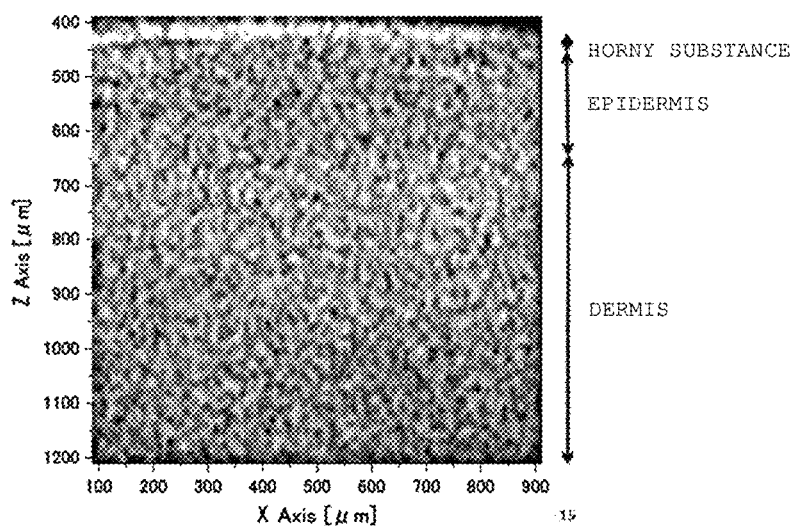
FIGS. 9A to 9C show examples of results of tomographic measurement relating to mechanical characteristics.
Figure 9B:
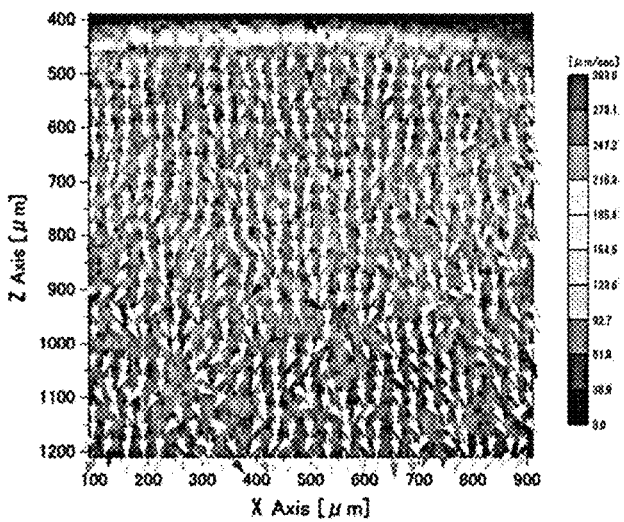
Figure 9C:
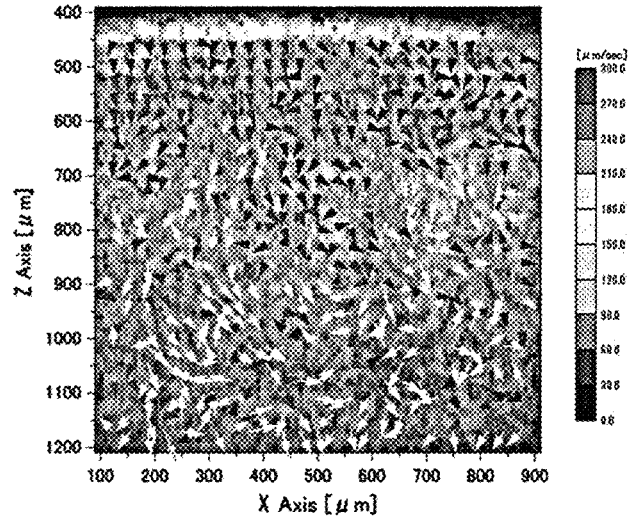

FIGS. 9A to 9C show examples of results of tomographic measurement relating to mechanical characteristics. Herein, results of applying a predetermined suction load to a site of skin to be measured, then unloading the site, and performing OCT measurement in the process of creep recovery of skin tissue are shown. FIG. 9A shows association between the skin tissue and a tomographic image. For convenience, FIG. 9A is shown in two-dimensional representation. A line with high intensity at about Z=450 μm corresponds to a skin surface, that is, a horny layer. A region with low intensity at 150 μm from the skin surface corresponds to epidermis, and a region with high intensity below the epidermis corresponds to dermis.

FIGS. 9B and 9C each show tomographic distribution of deformation rate vector of a predetermined time after unloading. FIG. 9B shows the tomographic distribution of 0.19 seconds after unloading, and FIG. 9C shows the tomographic distribution of 0.38 seconds after unloading. Comparison therebetween shows that the amount of decrease in the deformation quantity is larger near the surface (the epidermis and above) than the inside (beneath the dermis) of the skin.

FIG. 10 shows tomographic distribution of creep recovery time.

Strain rate tensors can be obtained by calculating space derivatives of the deformation rate vectors shown in FIGS. 9A to 9C. Strain rate distribution of the strain rate tensors is applied to the aforementioned expressions (12) and (13) to calculate the tomographic distribution τ(x,y,z) of creep recovery time shown in FIG. 10. For convenience, FIG. 10 is shown in two-dimensional representation. It can be observed in the tomographic distribution that the creep recovery time is short and elastic behavior is exhibited near the skin surface, while a region in which viscous behavior is exhibited is present in a deep layer of the skin. In this manner, the OCT measurement allows the mechanical characteristics of skin to be obtained.

(2) Blood Flow Velocity of Skin

A Doppler modulated signal is detected by the OCT, which enables calculation of blood flow velocity distribution of skin tissue. As described above, the EOPM 40 is provided in the reference arm 14 of the skin diagnosing device 1, which generates radio frequency carrier signals. The electric field $E'_r(t)$ of reference light is expressed by the following expression (14) in view of modulation angular frequency $\omega_m$ generated by the EOPM 40.

$$E'_r(t)=A(t)\exp\{i(-(\omega_c+\omega_r+\omega_m)t)\} \quad (14)$$

In the expression (14), A(t) represents amplitude, and $\omega_c$ represents the central angular frequency of the light source. $\omega_r$ represents a Doppler angular frequency generated at the resonant mirror 54 of the RSOD.

In a case where a flow field is present at a site to be measured, the electric field $E'_o(t)$ of object light is expressed by the following expression (15) in view of a Doppler angular frequency shift amount $\omega_d$ caused depending on the flow velocity.

$$E'_o(t)=\int A(t-\tau)R(z)\exp\{i(-(\omega_c+\omega_d)(t-\tau))\}d\tau \quad (15)$$

Since light intensity is the time average of the square of electric field intensity, a detected interference light intensity $I'_d(t)$ is expressed by the following expression (16)

$$\begin{aligned}I'_d(t) &= <|E'_r(t)+E'_o(t)|^2>_\tau \quad (16)\\ &= <|E'_r(t)|^2>_\tau + <|E'_o(t)|^2>_\tau + 2<|E'_r(t)^*E'_o(t)|>_\tau \\ &= I'_r + I'_o + 2\mathrm{Re}\Big(\int R(z)<A(t)A(t-\tau)>_\tau \exp\\ &\quad \{i(\omega_c+\omega_d)\tau\}\exp\{i(\omega_m+\omega_r-\omega_d)t\}d\tau\Big)\end{aligned}$$

In addition, a detected tomographic interference signal $I_d(x,y,z)$ is expressed by the following expression (17).

$$\begin{aligned}I_d(x,y,z) &= R(z)\otimes G(z)\exp\left(i\frac{2\pi}{\lambda_c}z\right)\exp(i(\omega_m+\omega_r-\omega_d)t) \quad (17)\\ &= R(z)\otimes\left(I'_m\exp\left\{-\frac{\sqrt{\ln 2}}{\Delta z^2}z^2\right\}\right)\exp(i(\omega_m+\omega_r-\omega_d)t)\end{aligned}$$

The angular frequency of an interference signal is expressed as $\omega_m+\omega_r-\omega_d$. The carrier angular frequency $\omega_m+\omega_r$ of the interference signal is used to detect the Doppler angular frequency shift amount $\omega_d$ generated depending on the blood flow velocity. The following expression (18) can then be computed by using the detected Doppler angular frequency shift amount $\omega_d$ to obtain the blood flow velocity v.

$$v = \frac{\omega_d \lambda_c}{4\pi n \cos\theta(x,y,z)} \quad (18)$$

In the expression (18), $\lambda_c$ represents the center wavelength of the light source, $\theta(x,y,z)$ represents an angle between the flow velocity direction and the beam incidence direction at coordinates (x,y,z). n represents the average refractive index in the inside of the skin.

Adjacent Autocorrelation Method

In this example, the technique of scanning in the depth direction (z axis direction) using the RSOD is employed as described above. In order to prevent degradation in flow velocity detection performance in this process, the Hilbert transform and the adjacent autocorrelation method are applied. Specifically, the adjacent autocorrelation method is applied to analytic signals (complex signals) Γ(t) obtained by applying the Hilbert transform to spatially adjacent interference signals. In this manner, a phase difference Δφ at certain coordinates is obtained, and a Doppler angular frequency shift amount G) depending on the blood flow velocity is detected.

Specifically, the respective interference signals are expressed as the following expression (19) where j-th and (j+1)-th analytic signals obtained by the application of the Hilbert transform are represented by $\Gamma_j$ and $\Gamma_{j+1}$, respectively.

$$\begin{aligned}\Gamma_j(t) &= s_j(t) + i\hat{s}_j(t) \quad (19)\\ &= A(t)\exp\{i(\omega_c+\omega_r(\lambda)+\omega_m)t+\omega_d t\}\\ \Gamma_{j+1}(t+\Delta T) &= s_{j+1}(t+\Delta T) + i\hat{s}_{j+1}(t+\Delta T)\\ &= A(t)\exp\{i(\omega_c+\omega_r(\lambda)+\omega_m)t+\omega_d(t+\Delta T)\}\end{aligned}$$

In the expression (19), s(t) represents the real part of the analytic signal Γ(t), and ŝ(t) represents the imaginary part thereof. ΔT represents a time interval between acquisitions of the j-th and the (j+1)-th interference signals, and A represents the amplitude (that is, backscatter intensity) of the interference signals.

In a case where phase modulation has not occurred in the electric field of object light ($\omega_d=0$), the phase difference of the interference signals is zero. The phase difference between interference signals of $\Gamma_j$ and $\Gamma_{j+1}$ corresponds to the phase shift amount $\omega_d \Delta T$ resulting from Doppler modulation caused depending on the blood flow velocity. Specifically, the Doppler angular frequency shift amount $\omega_d$ caused depending on the blood flow velocity is expressed as the following expression (20).

$$\begin{aligned}\omega_d &= \frac{1}{\Delta T}\cdot\omega_d\cdot\Delta T \quad (20)\\ &= \frac{1}{\Delta T}\cdot\Delta\phi\\ &= \frac{1}{\Delta T}\cdot(\phi_{j+1}-\phi_j)\\ &= \frac{1}{\Delta T}\cdot\arctan(\Gamma_{j+1}\Gamma_j^*)\\ &= \frac{1}{\Delta T}\cdot\arctan\left(\frac{s_{j+1}\hat{s}_j - s_j\hat{s}_{j+1}}{s_{j+1}s_j + \hat{s}_{j+1}\hat{s}_j}\right)\end{aligned}$$

Since the angle of deviation is $\Delta\varphi=\omega_d\Delta T$, the phase shift amount can be detected in a range of $-\pi$ to $\pi$. In addition, ensemble average can be performed on n interference signals according to the following expression (21) to improve the detection performance of the Doppler angular frequency shift amount $\omega_d$.

$$\omega_d = \frac{1}{\Delta T}\arctan\left(\frac{\text{Im}\left(\sum_{j=1}^{n}\Gamma_{j+1}\Gamma_j^*\right)}{\text{Re}\left(\sum_{j=1}^{n}\Gamma_{j+1}\Gamma_j^*\right)}\right) \quad (21)$$

The Doppler angular frequency shift amount $\omega_d$ obtained as described above is substituted into the expression (18) to calculate the blood flow velocity v.

A simulation test of blood flow velocity measurement using the OCT and results of the measurement will now be explained.

Figure 11A:
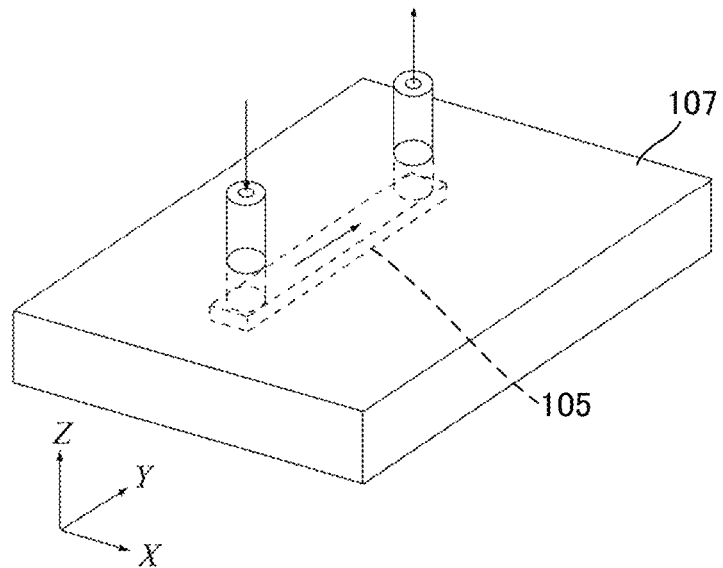
FIGS. 11A to 11C illustrate part of a device used for a blood flow velocity simulation test.
Figure 11B:
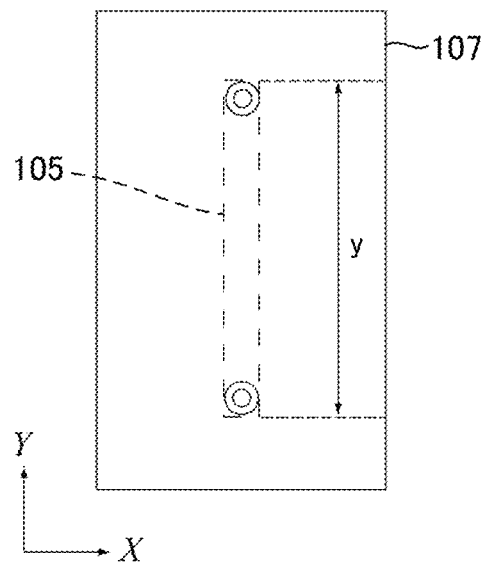
Figure 11C:
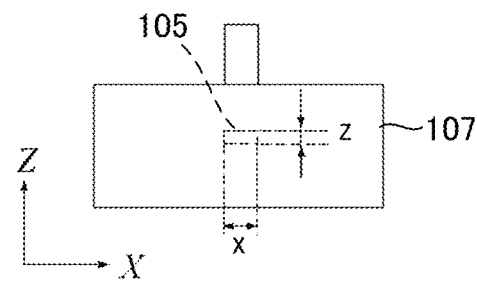
Figure 12A:
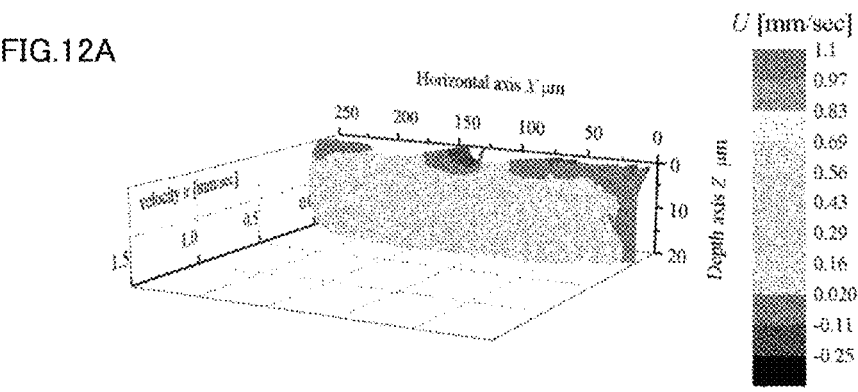
FIGS. 12A to 12D show tomographic distributions of flow velocities measured by using the OCT.
Figure 12B:
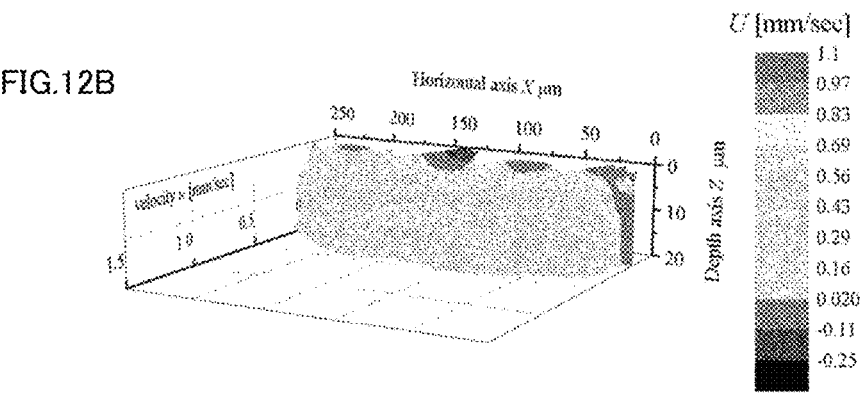
Figure 12C:
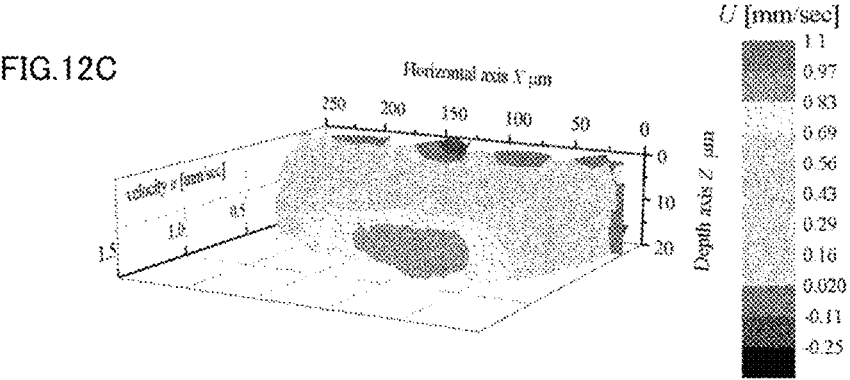
Figure 12D:
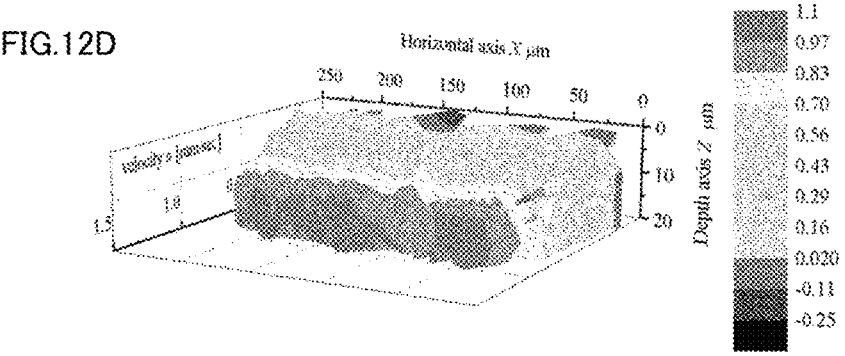

FIGS. 11A to 11C illustrate part of a device used for the blood flow velocity simulation test. FIG. 11A is a perspective view, FIG. 11B is a plan view, and FIG. 11C is a front view (as viewed in the Y direction). FIGS. 12A to 12D show tomographic distributions of flow velocities measured by using the OCT. FIGS. 12A to 12D show results with different set mean flow velocities U of red blood cell suspension, which will be described later.

In this simulation test, a microchannel 105 illustrated in FIGS. 11A to 11C was used. Specifically, the microchannel 105 was formed in a member 107 that is an imitation of skin, and a red blood cell suspension that is an imitation of blood was fed with pressure in the Y direction. The microchannel 105 had an opening size of (x×z)=(250 μm×40 μm) in XZ cross section, and a length y of 20 mm in the Y direction. The red blood cell suspension was prepared using blood drawn from a healthy human. Specifically, the drawn blood was centrifuged at a rotation speed of 3000 rpm for 20 minutes, a process of extracting a red blood cell layer washed with phosphate buffered saline (PBS) was repeated twice so that only red blood cells were extracted, and the red blood cells were diluted with citrate phosphate dextrose (CPD) solution to a hematocrit of 40%, which is equivalent to that of human blood.

The set mean flow velocities U in FIGS. 12A, 12B, 12C and 12D are 0.25 mm/s, 0.5 mm/s, 0.75 mm/s, and 1.0 mm/s, respectively. It can be seen in the blood flow velocity distributions in FIGS. 12A to 12D that the set values and the results of OCT measurement are consistent with each other. In addition, since the blood flow velocities increase toward the center of the channel, it can be observed that rheological properties of red blood cells appear. Thus, the test results show that the OCT enables measurement reflecting the rheological properties of red blood cells in the red blood cell suspension having the hematocrit equivalent to that of human blood, which is effective as a method of measurement of blood flow velocity distribution.

(3) Network of Blood Vessels of Skin

Figure 13:
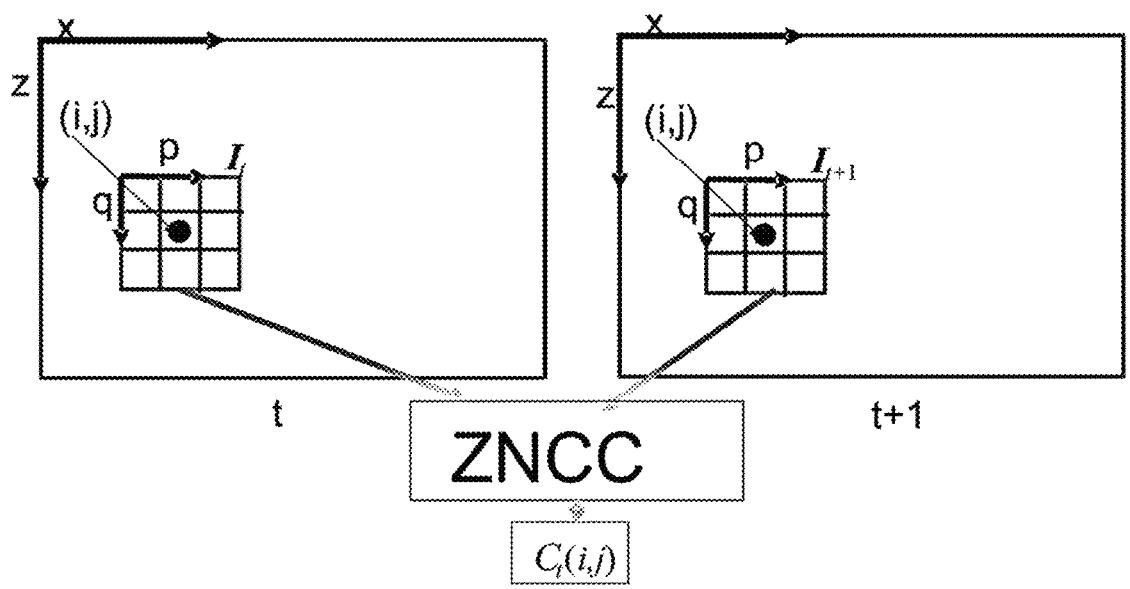
FIG. 13 is a schematic diagram illustrating a method for computing a network of blood vessels by using the OCT.

A network of blood vessels (shapes of blood vessels and changes in the shapes) can be calculated by computation of autocorrelation of tomographic images continuously taken by using the OCT. FIG. 13 is a schematic diagram illustrating a method for computing a network of blood vessels by using the OCT. The left part of FIG. 13 shows a tomographic image acquired at time t, and the right part of FIG. 13 shows a tomographic image acquired at time t+1. For convenience, FIG. 13 is shown in two-dimensional representation.

For calculation of a network of blood vessels, an interrogation region I is set in each of the continuously acquired tomographic images, and autocorrelation ZNCC in the region is computed. Specifically, a change in the image at the same coordinates (i,j) in the interrogation regions I is calculated as an autocorrelation value $C_t(i,j)$ in the following expression (22).

$$C_t(i,j) = \frac{\sum_q\sum_p(I_t(p,q)-\overline{I_t})(I_{t+1}(p,q)-\overline{I_{t+1}})}{\sqrt{\sum_q\sum_p(I_t(p,q)-\overline{I_t})^2 \times \sum_q\sum_p(I_t(p,q)-\overline{I_{t+1}})^2}} \quad (22)$$

In addition, the coordinates at which the autocorrelation value $C_t$ becomes lower than a predetermined determination threshold are obtained as part of the blood vessels. This utilizes the behavior of the autocorrelation value $C_t$ that is lowered by the blood flow in blood vessels. Noise reduction such as spatial frequency filtering or median filtering is performed on the thus obtained blood vessels data, to obtain a network of blood vessels. Note that such an autocorrelation process may performed in a superimposed manner on three or more tomographic images (time t+2, ..., t+N), so that the accuracy of calculation of the network of blood vessels is increased.

Figure 14A:
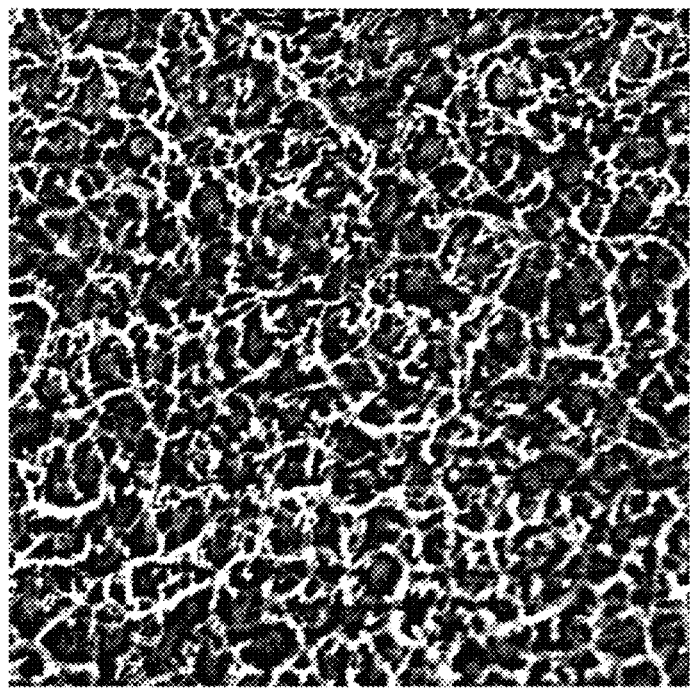
FIGS. 14A and 14B show results of calculation of a network of blood vessels.
Figure 14B:
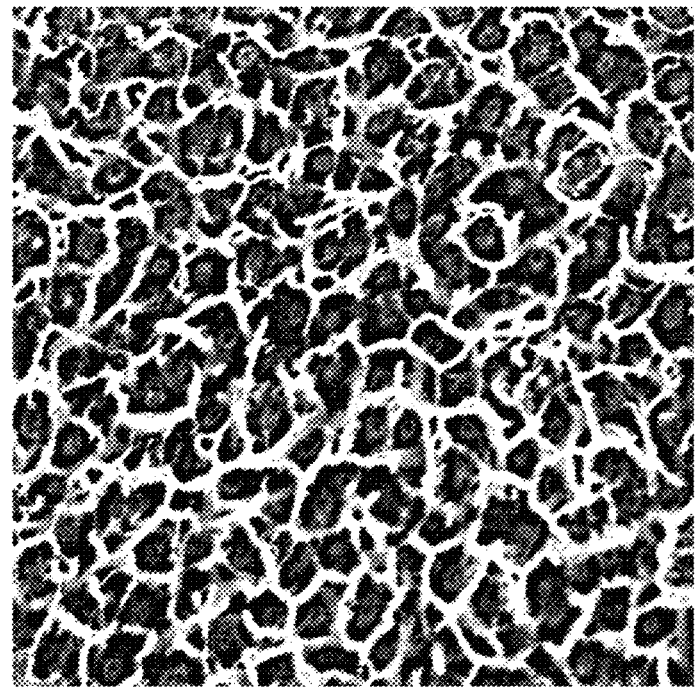

FIGS. 14A and 14B show results of calculation of the network of blood vessels. FIG. 14A shows a result of measurement of a predetermined position of a forearm in a normal condition. FIG. 14B shows a result of measurement of the same position in a case where a blood circulation promoter is applied. In FIGS. 14A and 14B, regions corresponding to the network of blood vessels, that is, the regions with low autocorrelation are shown with high intensity (white). It can be observed in these figures that the network of blood vessels is dilated by the blood circulation promoter. The measurement results show that a network of blood vessels can be calculated by using the OCT. Note that, when a network of blood vessels is interrupted by a load applied to skin, the visibility of the network of blood vessels using the OCT is lowered at the downstream of the interrupted position. When the load is removed, the visibility of the network of blood vessels using the OCT is recovered. Detection of such behavior allows evaluation of load responsiveness of skin and blood vessels, and thus the skin condition.

(4) Amount of Moisture of Skin

Water content distribution of skin tissue can be calculated by OCT measurement using two light sources with wavelength bands with different light absorption characteristics.

Figure 15:
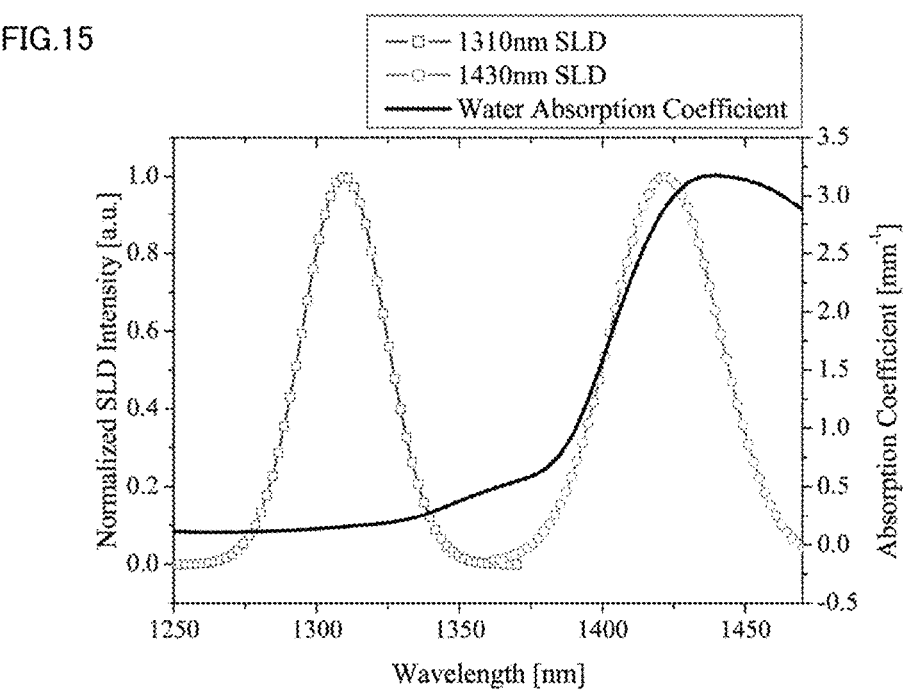
FIG. 15 is a graph showing light absorption characteristics of water.

FIG. 15 is a graph showing light absorption characteristics of water. FIG. 15 shows the relation between the wavelength and the intensity of light, and the relation between the wavelength of light and the light absorption coefficient of water. It can be seen in FIG. 15 that, at tissue having a high water content, backscattered light intensity of 1430-nm wavelength band light is attenuated by light absorbing action, but no influence of light absorbing action is observed on backscattered light intensity of 1310-nm wavelength band light. In this example, the difference in light absorption characteristics between the two wavelength bands is used for detection of water content distribution. Specifically, in this example, the light source with 1430-nm wavelength band in which moisture has light absorption characteristics and the light source with 1310-nm wavelength band in which moisture has no light absorption characteristics are used as described above.

Note that the backscattered light intensity $I^{\lambda_c}$ at a deep position z of skin is a convolution of a coherence function $G^{\lambda_c}(z)$ of the light source and the back-reflected light intensity $O^{\lambda_c}(x,y,z)$ inside the skin, which is expressed by the following expression (23).

$$I^{\lambda_c}(x, y, z) = I_{inc}^{\lambda_c} O^{\lambda_c}(x, y, z) \otimes \left| G^{\lambda_c}(z) \right| \cos\left(\frac{2\pi z}{\lambda_c}\right) \quad (23)$$

In the expression (23), $I_{inc}^{\lambda_c}$ represents the intensity of irradiation of the reference mirror and the object (skin), and the superscript $\lambda_c$ of the variables represents the center wavelength of incident light.

In a case where the back-reflected light intensity $O^{\lambda_c}(x,y,z)$ changes gradually over the coherence length, the coherence function $G^{\lambda_c}(z)$ can be approximated by a delta function, and a signal detected using the OCT can be expressed as $I^{\lambda_c} \approx I_{inc}^{\lambda_c} O^{\lambda_c}(x,y,z)$. Furthermore, since $O^{\lambda_c}(x,y,z)$ is dependent on incident light intensity distribution $I_o^{\lambda_c}(z)$ determined by the object lens, energy reflection coefficient $r^{\lambda_c}$ inside the tissue, attenuation by scattering, and attenuation by absorption, the back-reflected light intensity $O^{\lambda_c}(x,y,z)$ can be approximately formulated as an expression (24) below. Note that the energy reflection coefficient $r^{\lambda_c}$ of the skin surface is used so that the surface reflection is considered in the expression (24). In addition, average spatial variation of the energy reflection coefficient $R^{\lambda_c}$ inside the skin tissue is assumed to be small, and a scattering attenuation coefficient $\mu_s^{\lambda_c}$ (hereinafter also referred to as "scattering coefficient") and a absorption attenuation coefficient $\mu_a^{\lambda_c}$ (hereinafter also referred to as "absorption coefficient") are also used as principal parameters.

$$I^{\lambda_c}(z,y,z) \approx I_o^{\lambda_c}(z)(1 - R^{\lambda_c}(x,y))^2 r^{\lambda_c}(x,y,z) \times \exp[-2\int_0^x (\mu_s^{\lambda_c}(x,y,z') + \mu_a^{\lambda_c}(x,y,z'))dz'] \quad (24)$$

Furthermore, the following expressions (25) and (26) are obtained by assuming incident light intensity distribution $I_o^{\lambda_c}(z)$ in skin to be constant within the depth of field, taking a natural logarithm of the OCT signal of the expression (24), and obtaining a space derivative of the resulting OCT signal in the depth direction, which is the z direction.

$$\frac{\partial}{\partial z}\left[\ln(I^{1430}(x, y, z))\right] = -2\left(\mu_s^{1430}(x, y, z) + \mu_a^{1430}(x, y, z)\right) \quad (25)$$

$$\frac{\partial}{\partial z}\left[\ln(I^{1310}(x, y, z))\right] = -2\left(\mu_s^{1310}(x, y, z)\right) \quad (26)$$

Regarding the expression (26), the absorption coefficient $\mu_a^{1310}$ in the 1310-nm wavelength band is negligible since the molar absorption coefficient of water is very small, and tissue scattering coefficient distribution can be obtained from the attenuation coefficient $\mu_s^{1310}$. Furthermore, precalculation of scattering coefficient ratio κ expressed by the following expression (27) allows separate detection of the absorption coefficient $\mu_a^{1430}$.

$$\kappa = \frac{\mu_s^{1430}}{\mu_s^{1310}} \quad (27)$$

The left sides of the expressions (25) and (26) can be calculated by the moving least square method (MLSM). Thus, when the scattering coefficient ratio κ is known, the absorption coefficient $\mu_a^{1430}$ can be calculated by substituting the relation of $\mu_s^{1430}=\kappa \cdot \mu_s^{1310}$ into the expression (25) or (26) and calculating the equations simultaneously.

Figure 16A:
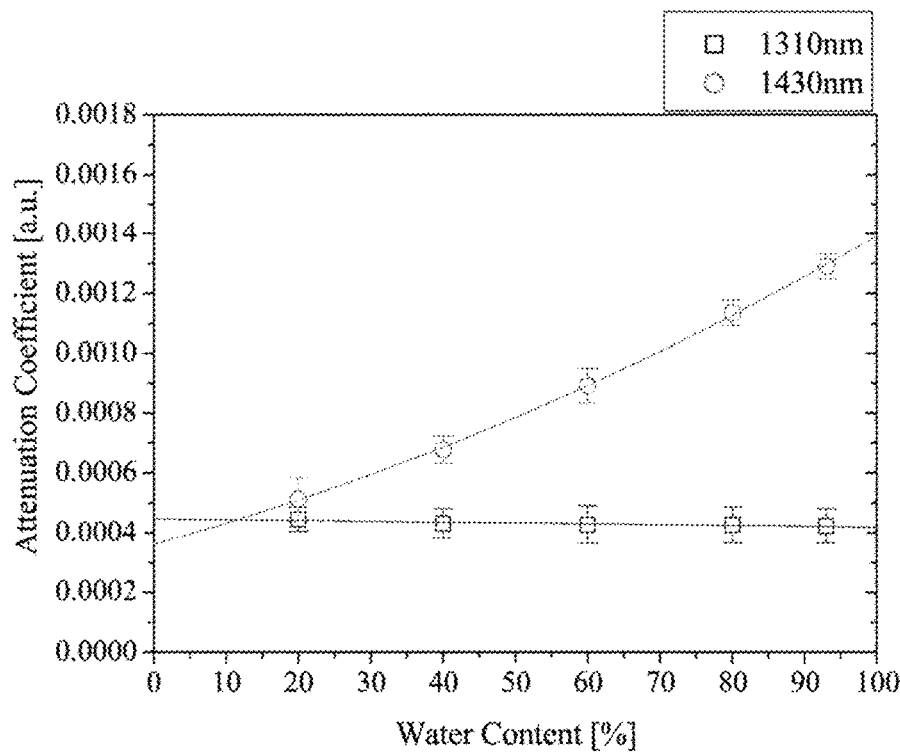
FIGS. 16A and 16B show the relation between light absorption characteristics of water and water content.
Figure 16B:
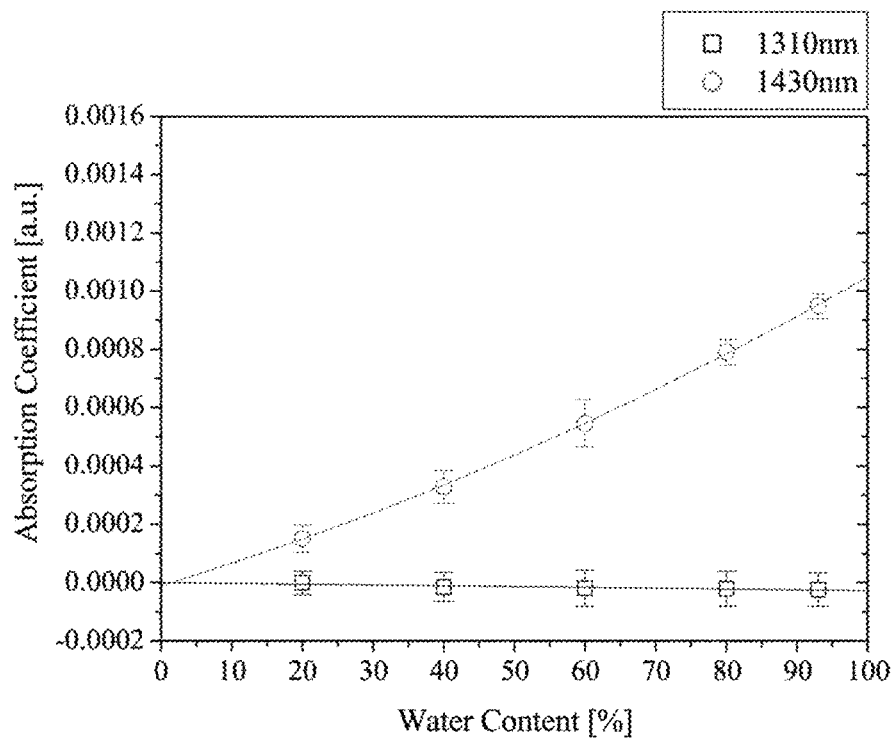

FIGS. 16A and 16B show the relation between the light absorption characteristics of water and water content. FIG. 16A shows the relation between the attenuation coefficient in each of the wavelength bands and the water content. In FIG. 16A, the horizontal axis represents the water content, and the vertical axis represents the attenuation coefficient. FIG. 16B shows the relation between the absorption coefficient in each of the wavelength bands and the water content. In FIG. 16B, the horizontal axis represents the water content, and the vertical axis represents the absorption coefficient.

As shown in FIG. 16A, when the water content of an object increases, the attenuation coefficient $\mu_s^{1430}$ of light in the 1430-nm wavelength band becomes larger but the attenuation coefficient $\mu_s^{1310}$ of light in the 1310-nm wavelength band changes little. This is because the former has the light absorption characteristics of water while the latter does not have the light absorption characteristics of water. The latter attenuation coefficient substantially corresponds to the attenuation by scattering alone.

Since the scattering coefficient ratio κ of the expression (27) is known, the relation of the absorption coefficient and the water content shown in FIG. 16B can be derived on the basis of the relation between the attenuation coefficient and the water content shown in FIG. 16A. Thus, the water content distribution of skin to be measured can be calculated by referring to the relation of FIG. 16B by using the absorption coefficient $\mu_a^{1430}$ calculated as described above.

Figure 17A:
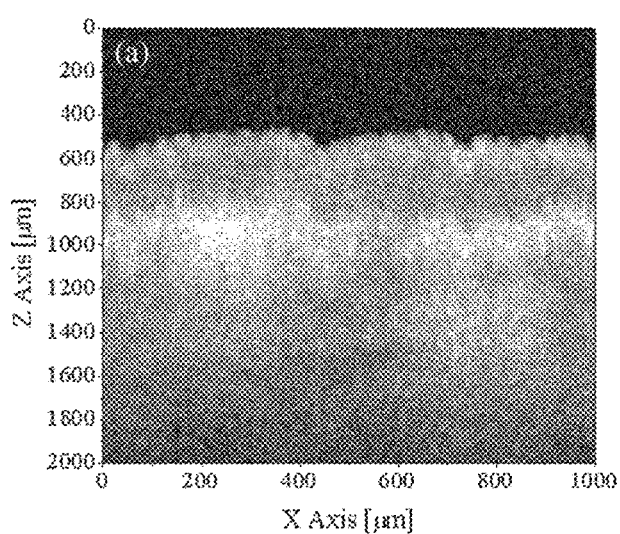
FIGS. 17A to 17C show processes of computing the amount of moisture in skin by using the OCT.
Figure 17B:
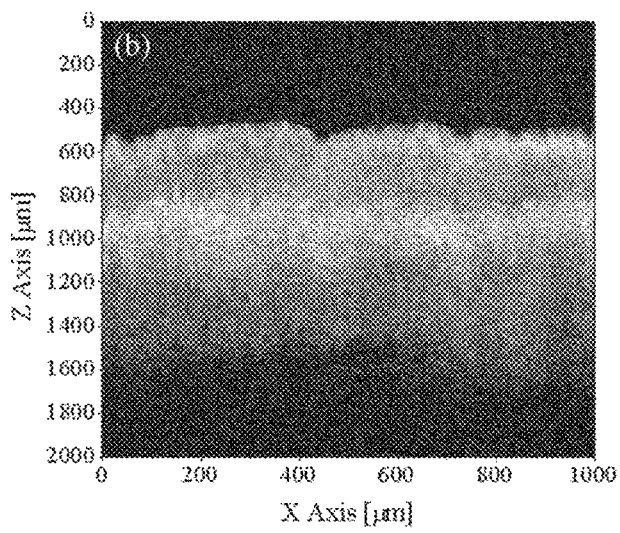
Figure 17C:
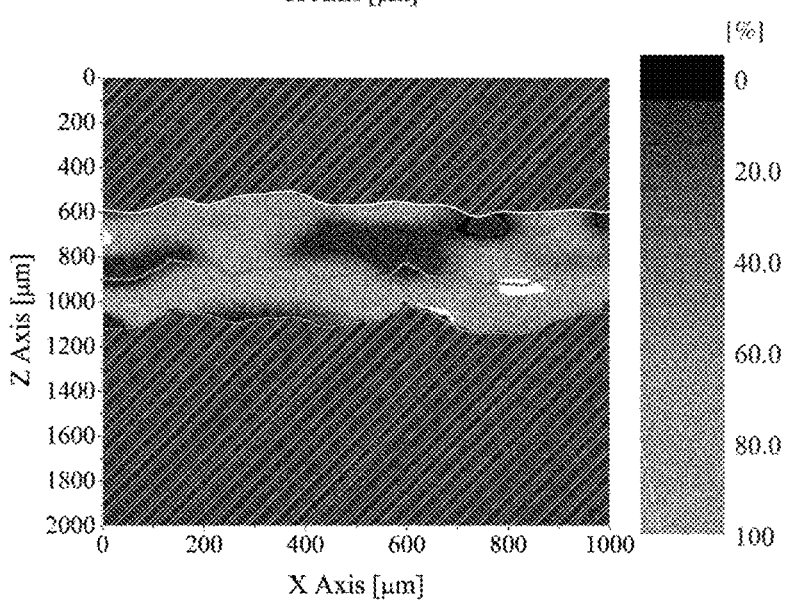

FIGS. 17A to 17C show processes of computing the amount of moisture in skin by using the OCT. FIG. 17A shows a tomographic image of the 1310-nm wavelength band, and FIG. 17B shows a tomographic image of the 1430-nm wavelength band. FIG. 17C shows water content distribution calculated on the basis of these tomographic images. For convenience, FIGS. 17A to 17C are shown in two-dimensional representation. In FIG. 17C, for convenience, the water content distribution is not displayed in regions where the S/N ratio is low.

In FIGS. 17A and 17B, a line with high intensity at about z=600 μm is deemed to correspond to a skin surface, and a line with high intensity at about z=900 μm is deemed to correspond to a boundary between a horny layer and an epidermal living cell layer. Comparison between FIGS. 17A and 17B show that the amount of attenuation in the depth direction is larger in the tomographic image of the 1430-nm wavelength band than the tomographic image of the 1310-nm wavelength band. The difference in the amount of attenuation is considered to be due to light absorption by water molecules present in the 1430-nm wavelength band.

It can be seen in FIG. 17C that distribution of water content is present in the x direction. In addition, the high water content in a high water content region is considered to be because of the presence of a sweat gland, and the low water content in a low water content region is considered to be because of the absence of a sweat gland. It can also be seen that the water content in the horny layer is lower than that in the epidermal living cell layer, and the water content tends to be higher at a deeper position.

The control computation unit 6 outputs information for skin diagnosis on the basis of the parameters including the mechanical characteristics, the blood flow velocity, the network of blood vessels, and the amount of moisture of skin. In other words, the control computation unit 6 calculates an evaluation value of skin and displays the evaluation value on the display device 74. The evaluation value may be one of levels into which the current skin condition is classified, for example. Five levels may be set, for example, such as level A (very good, excellent skin firmness, skin age: teens or lower), level B (good, good skin firmness, skin age: twenties), level C (average, not bad skin firmness, skin age: thirties), level D (certain aging alteration, sagging skin, skin age: forties), and level E (aging observed, noticeable sagging, skin age: fifties or higher).

There are various options in how to use these parameters for skin diagnosis. All of these parameters may be used for determination of the evaluation value, or the evaluation value may be determined on the basis of combination of some parameters. For example, the position and the shape of a network of blood vessels in skin may be calculated, and the evaluation may indicate that deterioration (aging) of skin has been advancing if the mechanical characteristics (elasticity, viscosity) at the position of the network of blood vessels are lower than predetermined reference values (standard values) (or if the strain rate is lower than a predetermined threshold). The elasticity of blood vessels is considered to be lost and metabolism is considered to be reduced when skin is deteriorated due to the influence of irradiation with ultraviolet rays and aging. This can be evaluated on the basis of OCT measurement.

In addition, such phenomena of a blood flow being interrupted when a load is applied to skin and the blood flow being restored when the load is reduced can be considered. In this case, a network of blood vessels will quickly change in response to a change in mechanical feature value if the skin tissue is in good condition, but the change of the network of blood vessels will be delayed (the following capability will be low) if the skin tissue is deteriorated. The change in mechanical feature value relates to the mechanical characteristics. On the basis of such finding, computation of the evaluation value may be based on the degree of a change in blood flow condition relative to a change in mechanical feature value.

In addition, it can be assumed that, as skin tissue deteriorates, the blood flow velocity in a network of blood vessels also lowers. More effective evaluation can thus be made in view of the blood flow velocity in skin tissue as described above. Furthermore, it can be assumed that, as skin tissue deteriorates, leakage of plasma components (body fluid) is abnormally enhanced and the number of capillaries themselves decreases owing to abnormality caused in the vascular structures of capillaries, which results in water content distribution different from normal distribution. More correct evaluation of deterioration (aging) of skin can thus be made by additional evaluation of the water content in skin tissue.

Specifically, the skin condition of a network of blood vessels and the vicinity thereof may be represented by a total of 15 points such as up to five points for the mechanical characteristics (elasticity and viscosity) (higher points being given as the elasticity/viscoelasticity is higher), up to five points for the blood flow velocity (higher points being given as the blood flow velocity is higher), and up to five points for water content (higher points being given as the water content is higher). Evaluation values for generally evaluating the condition (deterioration) of skin may then be set such as 12 to 15 points classified as level A, 9 to 11 points classified as level B, 6 to 8 points classified as level C, 5 to 7 points classified as level D, and 6 or lower points classified as level E.

Alternatively, the evaluation value may be calculated from the network of blood vessels and the mechanical characteristics only. The evaluation value may be calculated from the network of blood vessels, the mechanical characteristics, and the amount of moisture. Still alternatively, the evaluation value may be calculated on the basis of a change in mechanical feature value (strain rate) and a change in a network of blood vessels (such as the shapes of blood vessels). For example, a network of blood vessels having an abnormal structure due to an atopic rash, a pimple, a spot, or the like may be observed. In this case, it can be assumed that deformation of the network of blood vessels relative to a load applied to the skin is greater than a normal case. The evaluation value may be set on the basis of such finding.

The evaluation value calculated as described above may be displayed as tomographic distribution of skin on a screen. Alternatively, an average level may be displayed in a form of a comment as the evaluation value of the whole skin.

Figure 18:
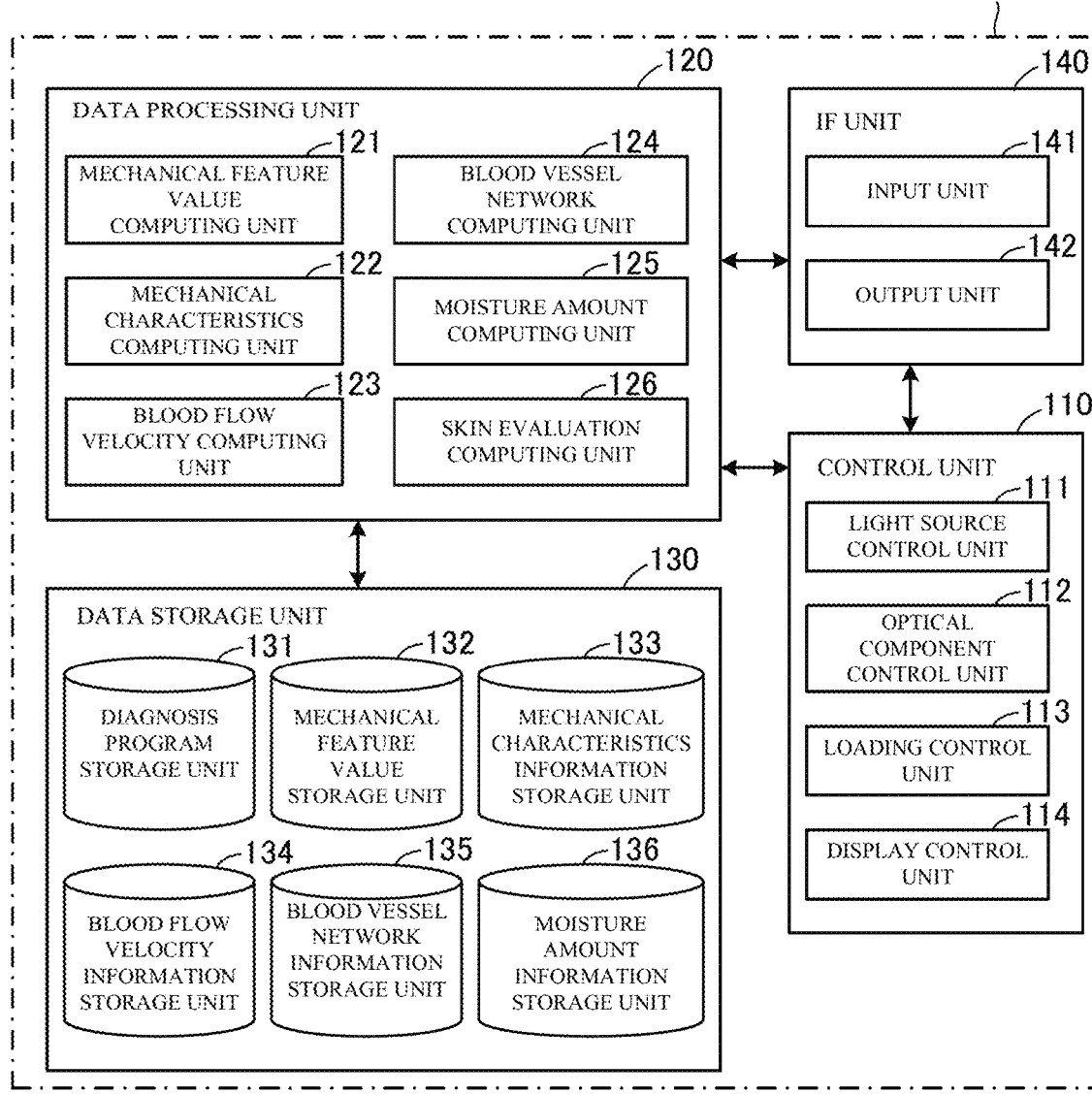
FIG. 18 is a functional block diagram of a control computation unit.

FIG. 18 is a functional block diagram of the control computation unit 6.

The control computation unit 6 includes a control unit 110, a data processing unit 120, a data storage unit 130, and an interface unit (IF unit) 140. The respective components cooperate on software to perform processing for skin diagnosis using the OCT measurement.

The control unit 110 includes a light source control unit 111, an optical mechanism control unit 112, a loading control unit 113, and a display control unit 114. The control unit 110 reads programs for drive control of the optical unit 2 from the data storage unit 130 and executes the programs to control respective devices and mechanisms. The light source control unit 111 controls driving of the light source 10. The optical mechanism control unit 112 controls driving of the optical mechanisms 4 and 26. The loading control unit 113 controls driving of the loading device 5. The display control unit 114 performs display processing of the display device 74.

The data processing unit 120 includes a mechanical feature value computing unit 121, a mechanical characteristics computing unit 122, a blood flow velocity computing unit 123, a blood vessel network computing unit 124, a moisture amount computing unit 125, and a skin evaluation computing unit 126. The data processing unit 120 reads programs for computing an evaluation value to be used for skin diagnosis from the data storage unit 130 and executes the programs to perform predetermined arithmetic processing.

The mechanical feature value computing unit 121 computes a mechanical feature value of skin described above by using a tomographic image obtained by using the OCT. The mechanical characteristics computing unit 122 computes the mechanical characteristics of the skin described above by using the obtained mechanical feature value. The blood flow velocity computing unit 123 computes the blood flow velocity of the skin described above by using an OCT signal. The blood vessel network computing unit 124 computes the network of blood vessels of the skin described above by using an OCT signal. The moisture amount computing unit 125 computes the amount of moisture (water content) of the skin described above by using an OCT signal. The skin evaluation computing unit 126 computes an evaluation value for skin diagnosis on the basis of changes or the like in the respective parameters, which are the mechanical feature value, the mechanical characteristics, the blood flow velocity, the network of blood vessels, and the amount of moisture, obtained as described above.

The data storage unit 130 includes a diagnosis program storage unit 131, a mechanical feature value storage unit 132, a mechanical characteristics information storage unit 133, a blood flow velocity information storage unit 134, a blood vessel network information storage unit 135, and a moisture amount information storage unit 136. The diagnosis program storage unit 131 stores control programs for controlling the respective components of the optical unit 2 and computation programs for evaluation of skin condition.

The mechanical feature value storage unit 132 temporarily stores data relating to the mechanical feature value obtained by the mechanical feature value computing unit 121. The mechanical characteristics information storage unit 133 temporarily stores data relating to the mechanical characteristics obtained by the mechanical characteristics computing unit 122. The blood flow velocity information storage unit 134 temporarily stores data relating to the blood flow velocity obtained by the blood flow velocity computing unit 123. The blood vessel network information storage unit 135 temporarily stores data relating to the network of blood vessels obtained by the blood vessel network computing unit 124. The moisture amount information storage unit 136 temporarily stores data relating to the amount of moisture (water content) obtained by the moisture amount computing unit 125.

The IF unit 140 includes an input unit 141 and an output unit 142. The input unit 141 receives detected data transmitted from the optical unit 2 and instruction commands and the like input by the user using the input device 70, and sends the received data and commands to the control unit 110 and the data processing unit 120. The output unit 142 outputs control command signals computed by the control unit 110 toward the optical unit 2. The output unit 142 also outputs data for display of results of computation of the data processing unit 120 toward the display device 74.

Next, a flow of specific processing performed by the control computation unit 6 will be explained.

Figure 19:
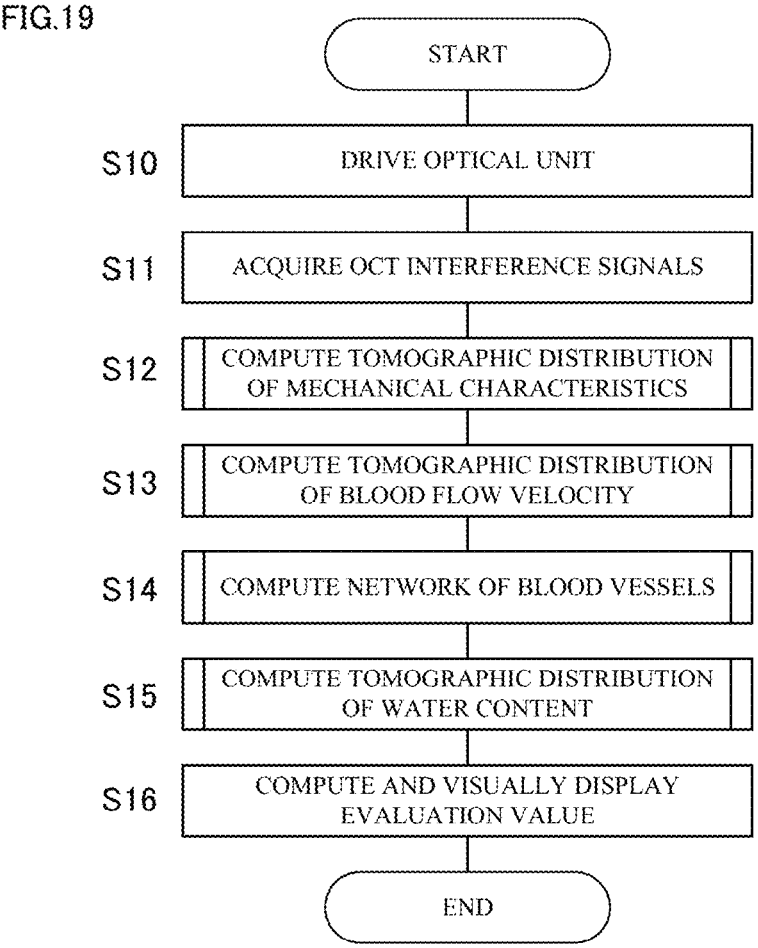
FIG. 19 is a flowchart illustrating a flow of a skin diagnosis process performed by the control computation unit.

FIG. 19 is a flowchart illustrating a flow of a skin diagnosis process performed by the control computation unit 6. The control computation unit 6 first drives the optical unit 2 (S10). The loading control unit 113 drives the loading device 5 and controls the load applied to skin S, the light source control unit 111 controls light emission from the light source 10, and the optical mechanism control unit 112 controls operation of the optical mechanisms 4 and 26. The control computation unit 6 continuously acquires optical interference signals in the OCT while the load is applied to the skin S (S11). Subsequently, the control computation unit 6 computes tomographic distributions of the parameters described above of the skin S by using the optical interference signals.

Specifically, the mechanical feature value computing unit 121 computes deformation vectors of skin tissue, and the mechanical characteristics computing unit 122 computes tomographic distribution of the mechanical characteristics (S12). The blood flow velocity computing unit 123 computes tomographic distribution of the blood flow velocity (S13), the blood vessel network computing unit 124 computes the network of blood vessels (S14), and the moisture amount computing unit 125 computes tomographic distribution of water content (S15). The skin evaluation computing unit 126 then associates the computation results of these parameters at the cross-sectional position of the skin S to compute the evaluation value of the skin condition (S16). The calculation of the evaluation value is as described above. The display control unit 114 displays the evaluation value on a screen.

Figure 20:
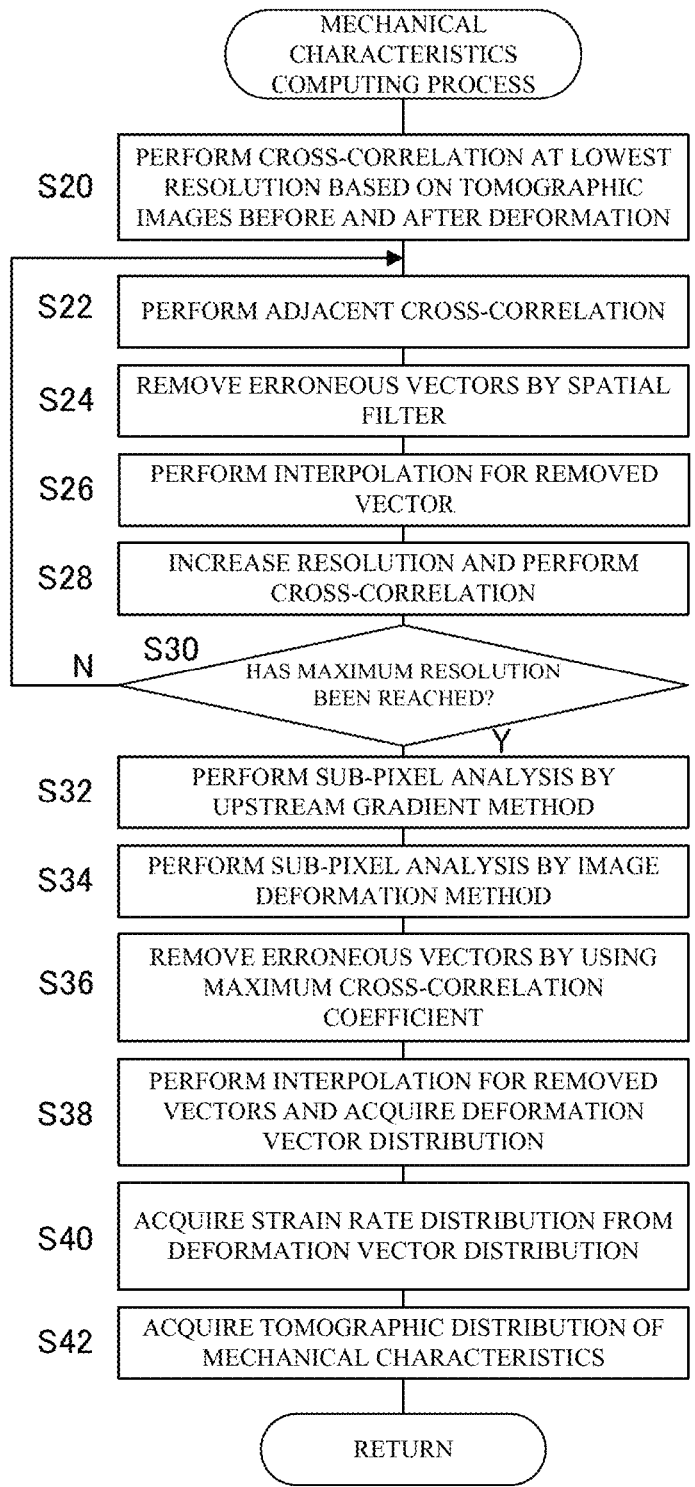
FIG. 20 is a flowchart illustrating a mechanical characteristics computing process in S12 of FIG. 19 in detail.

FIG. 20 is a flowchart illustrating the mechanical characteristics computing process in S12 of FIG. 19 in detail. The mechanical feature value computing unit 121 performs processing by the recursive cross-correlation method on the basis of tomographic images acquired before and after deformation by using the OCT. In this process, the mechanical feature value computing unit 121 first performs cross-correlation at minimum resolution (an interrogation region of a maximum size), and obtains correlation coefficient distributions (S20). Subsequently, the mechanical feature value computing unit 121 computes a product of adjacent correlation coefficient distributions by adjacent cross-correlation multiplication (S22). At this point, the mechanical feature value computing unit 121 removes erroneous vectors by a spatial filter such as a standard deviation filter (S24), and performs interpolation for the removed vectors by the least-squares method or the like (S26). Subsequently, the mechanical feature value computing unit 121 reduces the interrogation region in size to increase the resolution, and continue the cross-correlation (S28). Thus, cross-correlation is performed on the basis of a reference vector at low resolution. If the resolution at this point has not reached a predetermined maximum resolution (S30: N), the mechanical feature value computing unit 121 returns to S22.

The mechanical feature value computing unit 121 repeats the processing in S22 to S28, and when the cross-correlation at the maximum resolution is completed (S30: Y), performs sub-pixel analysis. Specifically, the mechanical feature value computing unit 121 computes a sub-pixel displacement by the upstream gradient method on the basis of the distribution of deformation vectors at the maximum resolution (the interrogation region of the minimum size) (S32). The mechanical feature value computing unit 121 then computes a sub-pixel deformation quantity by the image deformation method on the basis of the obtained sub-pixel displacement (S34). Subsequently, the mechanical feature value computing unit 121 removes erroneous vectors by filtering using a maximum cross-correlation value (S36), and performs interpolation for the removed vectors by the least-squares method or the like (S38). The mechanical feature value computing unit 121 then differentiates the thus obtained deformation vectors with respect to time to calculate tomographic distribution of deformation rate vector of the tomographic image. The mechanical feature value computing unit 121 then differentiates the deformation rate vectors with respect to space to obtain strain rate distribution (S40). The mechanical characteristics computing unit 122 computes tomographic distribution of the mechanical characteristics (elasticity or viscoelasticity) on the basis of the strain rate distribution (S42).

Figure 21:
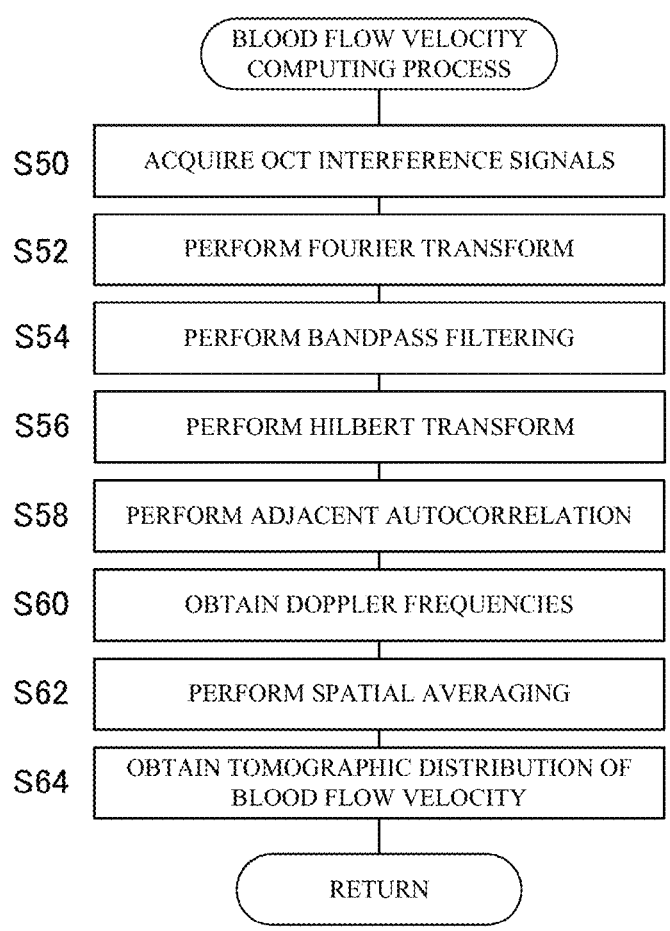
FIG. 21 is a flowchart illustrating a blood flow velocity computing process in S13 of FIG. 19 in detail.

FIG. 21 is a flowchart illustrating the blood flow velocity computing process in S13 of FIG. 19 in detail. The blood flow velocity computing unit 123 acquires OCT interference signals (S50), and performs Fourier transform (FFT) (S52). Subsequently, the blood flow velocity computing unit 123 performs bandpass filtering based on a carrier frequency to improve the S/N ratio of the signals (S54), and then performs Hilbert transform (S56). The blood flow velocity computing unit 123 performs adjacent autocorrelation on analytic signals obtained by the Hilbert transform to obtain phase differences (S58), and obtain Doppler frequencies (S60). The blood flow velocity computing unit 123 performs spatial averaging of the obtained Doppler frequencies to the pixel size (S62), and calculates tomographic distribution of the blood flow velocity (S64).

Figure 22:
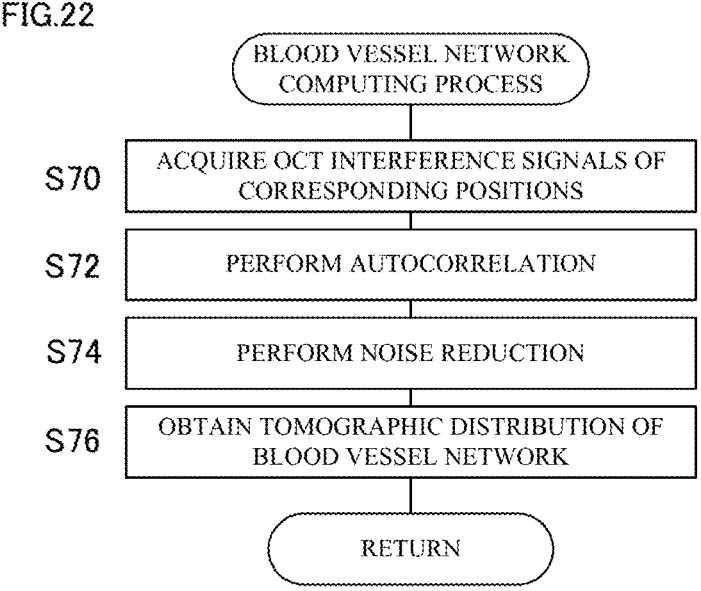
FIG. 22 is a flowchart illustrating a blood vessel network computing process in S14 of FIG. 19 in detail.

FIG. 22 is a flowchart illustrating the blood vessel network computing process in S14 of FIG. 19 in detail. The blood vessel network computing unit 124 acquires optical interference signals of corresponding positions by using the OCT (S70), and performs autocorrelation (S72). Subsequently, the blood vessel network computing unit 124 performs noise reduction such as spatial frequency filtering (S74), and obtains tomographic distribution of network of blood vessels (S76).

Figure 23:
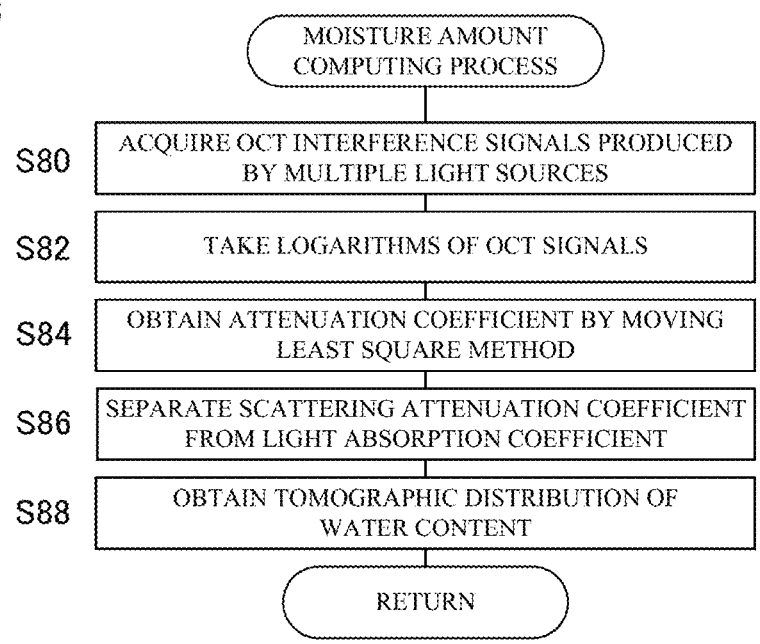
FIG. 23 is a flowchart illustrating a moisture amount computing process in S15 of FIG. 19 in detail.

FIG. 23 is a flowchart illustrating the moisture amount computing process in S15 of FIG. 19 in detail. The moisture amount computing unit 125 acquires OCT interference signals produced by a plurality of light sources 32 and 34 (S80). As described above, the light source 32 is a light source with 1310-nm wavelength band not having the light absorption characteristics and the light source 34 is a light source with 1430-nm wavelength band having the light absorption characteristics. The moisture amount computing unit 125 then takes natural logarithms of the OCT signals (S82), and obtains space derivatives thereof. Subsequently, the moisture amount computing unit 125 calculates the attenuation coefficient by the moving least square method as described above, (S84), separates the absorption coefficient (S86), and obtains tomographic distribution of water content (S88).

The description of the present invention given above is based on illustrative examples. It will be obvious to those skilled in the art that the present invention is not limited to the particular examples but various modifications could be further developed within the technical idea underlying the present invention.

In the example described above, the suction type load mechanism with the vacuum pump is presented as the loading device for applying predetermined deformation energy (load) to skin. In a modification, a load mechanism such as a piezoelectric device that applies stress through contact may be employed.

Figure 24:
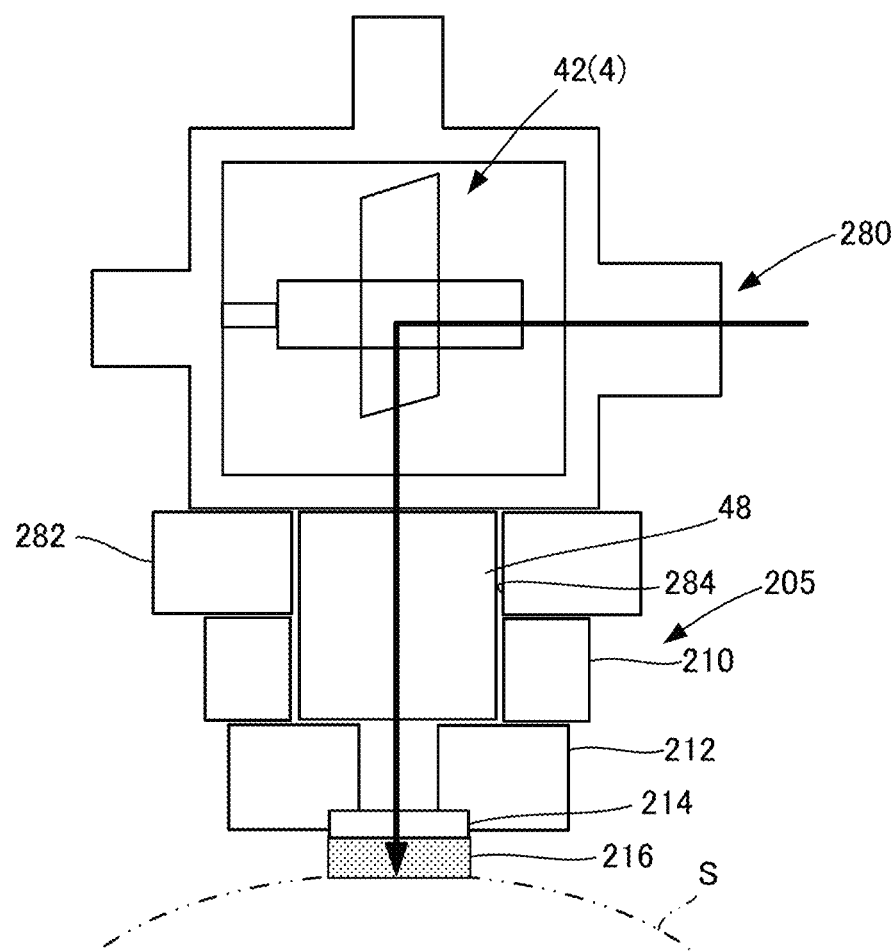
FIG. 24 is a diagram schematically illustrating a configuration of a loading device according to a modification.

FIG. 24 is a diagram schematically illustrating a configuration of a loading device according to a modification. In FIG. 24, components that are substantially the same as those in the example above will be represented by the same reference numerals.

A loading device 205 has a configuration of such a type that applies a pressing load to a site of skin S to be measured. A probe 280 for skin diagnosis is provided at an end of an optical mechanism 4. An upper half part of the probe 280 functions as the optical mechanism 4, and a lower half part thereof functions as the loading device 205. An internal passage 284 is formed to extend through a body 282 of the probe 280 in the axial direction, and an object lens 48 is located on the axis of the internal passage 284. The loading device 205 includes a piezoelectric device 210 (piezoelectric element) and an indenter 212 mounted on the body 282. The piezoelectric device 210 and the indenter 212 each have a cylindrical shape, and are located coaxially relative to the body 282. A parallel flat substrate 214 is provided at a lower end opening of the indenter 212, and an elastomer 216 is further provided on a lower face of the parallel flat substrate 214. The parallel flat substrate 214 is made of a synthetic quartz material, which is excellent in heat resistance and impact resistance. The elastomer 216 is a light-transmitting elastic member with a known material constant, which can transfer the pressing load from the piezoelectric device 210 to skin S.

A piezoelectric sensor (which functions as a "load detecting unit") is mounted on the elastomer 216. The piezoelectric sensor detects deformation of the elastomer 216 to detect a load applied by the piezoelectric device 210. Specifically, a load detected through deformation of the elastomer 216 can be detected as the load (pressure) applied to the surface of the skin S. As shown by an arrow in FIG. 24, object light from the optical unit 2 is transmitted by the object lens 48, the parallel flat substrate 214, and the elastomer 216, and directed to the skin S, and light reflected by the skin S returns to the optical unit 2 through the path in reverse direction.

Such a configuration allows detection of a change in the load applied during the process of deformation of skin S in real time, and allows the mechanical feature value and the blood flow condition in response to the load change to be calculated simultaneously. The evaluation value for skin diagnosis may be computed on the basis of the calculation results.

Although not mentioned in the above example, the strain rate distribution obtained in S40 of FIG. 20 may be tomographically visualized on the display device 74. Similarly, the blood flow velocity distribution obtained in S64 of FIG. 21 may be tomographically visualized on the display device 74.

While an example in which three-dimensional tomographic images are acquired by using the OCT is presented in the example described above, two-dimensional tomographic images may alternatively be acquired. Specifically, deformation vectors or deformation rate vectors as the displacement related vectors may be processed as two-dimensional data.

Although not mentioned in the example described above, an amplitude value of the strain rate or a time lag (phase lag) of the strain rate may be employed as the "mechanical feature value." Specifically, in the dynamic viscoelastic method as an example, the strain rate varies between a positive value and a negative value in the process in which application and relaxation of stress are repeated. The strain rate also varies following the variation of the load. In this regard, the magnitude (amplitude value) of the variation of the strain rate and the following capability (responsiveness) of the variation of the strain rate relative to the variation of the load tend to change depending on the skin condition. Thus, tomographic distribution of the amplitude value or the time lag (phase lag) of the strain rate may be computed.

Alternatively, a median of periodical variation of the strain rate may be employed as the "mechanical feature value." Specifically, in the dynamic viscoelastic method described above as an example, the strain rate varies between a positive value and a negative value in the process in which application and relaxation of stress are repeated. The center of variation of the strain rate tends to be slightly deviated from zero owing to the balance between viscous force and elastic force. In addition, the amount of deviation tends to change depending on the skin condition. Thus, tomographic distribution of the amount of deviation of the variation center (median) of the strain rate may be computed.

In the example described above, the suction type load mechanism with the vacuum pump is presented as the loading device for applying predetermined deformation energy (load) to skin. In a modification, a loading device that applies a load (exciting force) to skin in a non-contact manner by ultrasonic waves (sound pressure), photoacoustic waves, electromagnetic waves, or the like may be employed.

Although not mentioned in the example described above, the control unit 110 and the data processing unit 120 illustrated in FIG. 18 may be included in individual devices (such as personal computers).

Figure 25A:
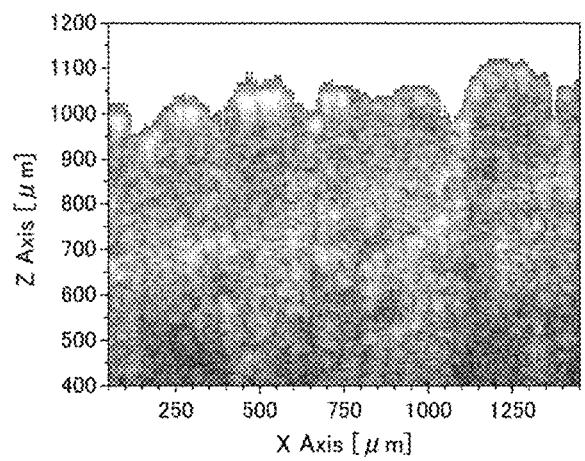
FIGS. 25A to 25C show OCT images of a side of an inwardly flexed human forearm.
Figure 25B:
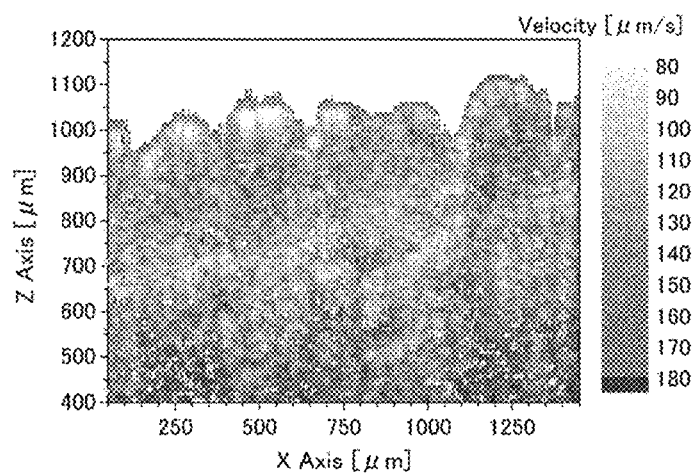
Figure 25C:
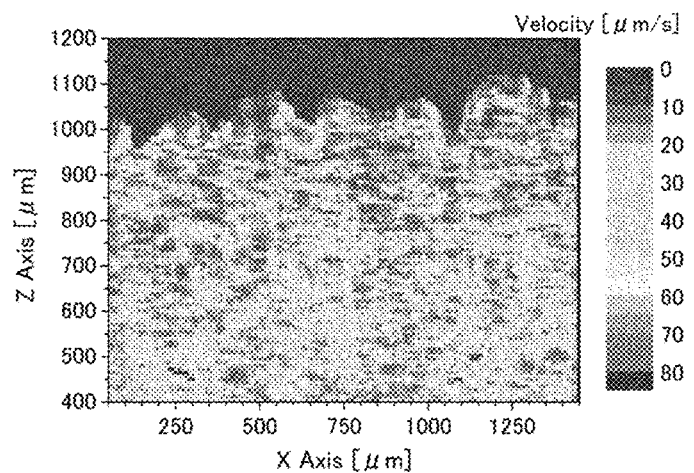
Figure 26A:
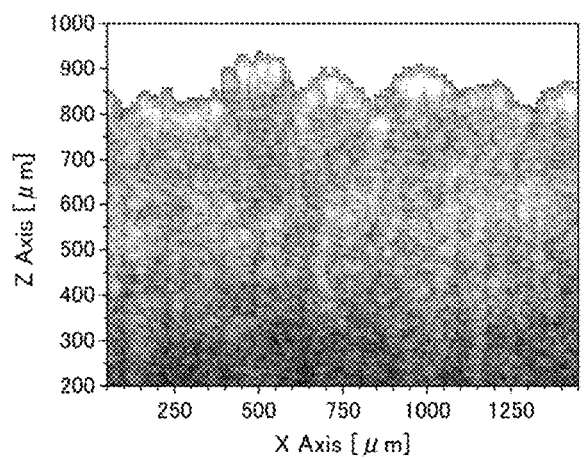
FIGS. 26A to 26C show OCT images of a side of an inwardly flexed human forearm.
Figure 26B:
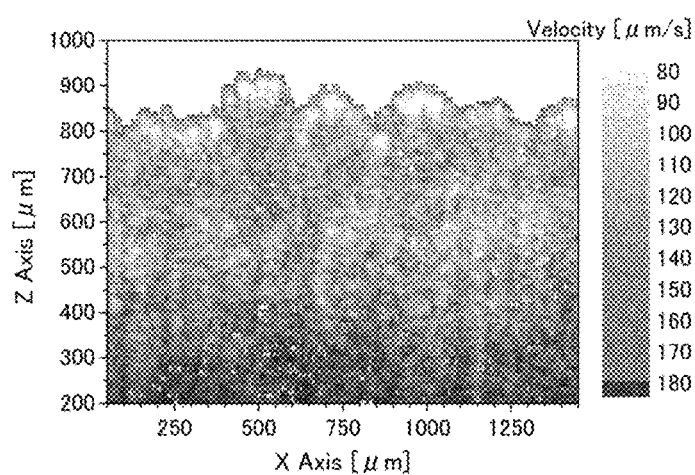
Figure 26C:
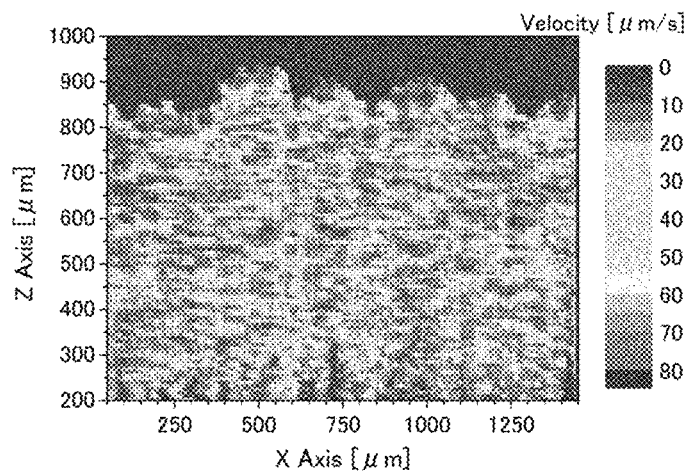

FIGS. 25A to 25C and 26A to 26C show OCT images of a side of an inwardly flexed human forearm. FIGS. 25A to 25C show tomographic measurement results in a normal condition, and FIGS. 26A to 26C show tomographic measurement results with use of a tourniquet. FIGS. 25A and 26A show OCT images. FIGS. 25B and 26B show maximum values of the blood flow velocity at predetermined time superimposed on the OCT images of FIGS. 25A and 26A, respectively, and FIGS. 25C and 26C show time averages of the blood flow velocity. Portions at about Z=1000 μm correspond to skin surfaces, that is, horny layers.

It can be observed in these results of tomographic measurement that the blood flow velocity of blood rising from a dermis upper layer to under an epidermis is lower in the avascularized state shown in FIGS. 26A to 26C than in the normal state shown in FIGS. 25A to 25C. It can be seen that less blood reaches to ends of capillaries in the avascularized state, and the measurement results can be evaluated as being consistent with the actual conditions.

The present invention is not limited to the above-described examples and modifications only, and the components may be further modified to arrive at various other examples without departing from the scope of the invention. Various other examples may be further achieved by combining, as appropriate, a plurality of structural components disclosed in the above-described example and modifications. Furthermore, one or some of all of the components exemplified in the above-described example and modifications may be left unused or removed.

What is claimed is:

1. A skin diagnosing device for diagnosing skin, comprising:
   an optical unit including an optical system that uses optical coherence tomography;
   an optical mechanism to guide light from the optical unit to the skin to scan the skin;
   a loading device to apply predetermined deformation energy to the skin;
   a control computation unit to compute tomographic distribution of predetermined status values relating to the skin by controlling driving of the loading device and the optical mechanism and processing optical interference signals output from the optical unit in response to the driving, to compute a mechanical characteristics of the skin on the basis of the tomographic distribution; and
   a display device to display the mechanical characteristics of the skin, wherein
   the predetermined status values comprise a change in the mechanical characteristics and a change in a blood flow condition of the skin at a cross-sectional position of the skin
   wherein the mechanical characteristics comprises elasticity or viscoelasticity,
   wherein when the elasticity or the viscoelasticity in a vicinity of blood vessels is lower than a predetermined reference value, a deterioration of the skin is diagnosed and displayed on the display device,
   wherein the control computation unit computes a degree of deformation of a network of blood vessels as a degree of the change in the blood flow condition.

2. A skin diagnosing device for diagnosing skin, comprising:
   an optical unit including an optical system that uses optical coherence tomography;
   an optical mechanism to guide light from the optical unit to the skin to scan the skin;
   a loading device to apply predetermined deformation energy to the skin;
   a control computation unit to compute tomographic distribution of predetermined status values relating to the skin by controlling driving of the loading device and the optical mechanism and processing optical interference signals output from the optical unit in response to the driving, to compute a mechanical characteristics of the skin on the basis of the tomographic distribution; and
   a display device to display the mechanical characteristics of the skin, wherein
   the predetermined status values comprise a change in the mechanical characteristics and a change in a blood flow condition of the skin at a cross-sectional position of the skin
   wherein the mechanical characteristics comprises elasticity or viscoelasticity,
   wherein when the elasticity or the viscoelasticity in a vicinity of blood vessels is lower than a predetermined reference value, a deterioration of the skin is diagnosed and displayed on the display device,
   wherein the control computation unit computes a degree of change in a blood flow velocity as a degree of the change in the blood flow condition.

3. The skin diagnosing device according to claim 1, wherein the control computation unit computes a displacement related vector associated with the cross-sectional position of the skin as the mechanical feature value on the basis of tomographic image data acquired by processing optical interference signals, and computes a degree of the change in the blood flow condition relative to a change in the displacement related vector.

4. The skin diagnosing device according to claim 1, wherein the control computation unit further computes a change in water content of the skin resulting from application of the deformation energy in association with the cross-sectional position of the skin, and computes a degrees of changes in the blood flow condition and the water content relative to the change in the mechanical characteristics.

5. A skin condition outputting method by using the skin diagnosing device of claim 1, comprising:
   a step of acquiring a tomographic image of the skin by using the optical coherence tomography;
   a step of computing the mechanical characteristics and the blood flow condition of the skin on the basis of the tomographic image; and
   a step of acquiring the mechanical characteristics and the blood flow condition at the cross-sectional position of the skin, and outputting the information.

6. The skin diagnosing device according to claim 1, further comprising a computer-readable recording medium having recorded thereon a program for causing the control computation unit to implement:
   a function of acquiring a tomographic image of the skin by using the optical coherence tomography;
   a function of computing the mechanical characteristics and the blood flow condition of the skin on the basis of the tomographic image; and
   a function of acquiring information for diagnosing the skin by associating the mechanical characteristics and the blood flow condition at the cross-sectional position of the skin, and outputting the information.

7. The skin diagnosing device according to claim 2, wherein the control computation unit computes a displacement related vector associated with the cross-sectional position of the skin as the mechanical feature value on the basis of tomographic image data acquired by processing optical interference signals, and computes a degree of the change in the blood flow condition relative to a change in the displacement related vector.

8. The skin diagnosing device according to claim 2, wherein the control computation unit further computes a change in water content of the skin resulting from application of the deformation energy in association with the cross-sectional position of the skin, and computes a degrees of changes in the blood flow condition and the water content relative to the change in the mechanical characteristics.

9. A skin condition outputting method by using the skin diagnosing device of claim 2, comprising:
   a step of acquiring a tomographic image of the skin by using the optical coherence tomography;
   a step of computing the mechanical characteristics and the blood flow condition of the skin on the basis of the tomographic image; and
   a step of acquiring the mechanical characteristics and the blood flow condition at the cross-sectional position of the skin, and outputting the information.

10. The skin diagnosing device according to claim 2, further comprising a computer-readable recording medium having recorded thereon a program for causing the control computation unit to implement:
    a function of acquiring a tomographic image of the skin by using the optical coherence tomography;
    a function of computing the mechanical characteristics and the blood flow condition of the skin on the basis of the tomographic image; and
   a function of acquiring information for diagnosing the skin by associating the mechanical characteristics and the blood flow condition at the cross-sectional position of the skin, and outputting the information.

* * * * *